(12) United States Patent
Huebert et al.

(10) Patent No.: US 7,884,186 B2
(45) Date of Patent: Feb. 8, 2011

(54) ISOTOPICALLY LABELED TRAPPING AGENT AND METHOD FOR IDENTIFYING REACTIVE METABOLITES

(75) Inventors: Norman D. Huebert, Glenmoore, PA (US); Zhengyin Yan, Dresher, PA (US)

(73) Assignee: Janssen Pharmaceutica NV, Beerse (BE)

( * ) Notice: Subject to any disclaimer, the term of this patent is extended or adjusted under 35 U.S.C. 154(b) by 806 days.

(21) Appl. No.: 11/860,056

(22) Filed: Sep. 24, 2007

(65) Prior Publication Data

US 2008/0081349 A1 Apr. 3, 2008

Related U.S. Application Data

(60) Provisional application No. 60/827,526, filed on Sep. 29, 2006.

(51) Int. Cl.
*A61K 38/06* (2006.01)
(52) U.S. Cl. .................................................. 530/331
(58) Field of Classification Search ....................... None
See application file for complete search history.

(56) References Cited

U.S. PATENT DOCUMENTS

| 6,197,575 | B1 | 3/2001 | Griffith et al. |
| 2002/0034729 | A1 | 3/2002 | Avery et al. |
| 2003/0180962 | A1 | 9/2003 | Kaplan et al. |
| 2005/0186651 | A1 | 8/2005 | Gan et al. |
| 2005/0287623 | A1 | 12/2005 | Yan et al. |

FOREIGN PATENT DOCUMENTS

| EP | 1150120 A2 | 10/2001 |
| WO | WO 91/08762 A1 | 6/1991 |
| WO | WO 03/027682 A2 | 4/2003 |
| WO | WO 2006/012154 | 2/2006 |

OTHER PUBLICATIONS

Yan, Zhengyin et al, "Stable-Isotope Trapping and High-Throughput Screenings of Reactive Metabolites Using the Isotope MS Signature," Analytical Chemistry (2004), 76(23), 6835-6847.*
Yan, Zhengyin et al: "Stable-isotope trapping and high-throughput screenings of reactive metabolites using the isotope MS signature." Analytical Chemistry Dec. 1, 2004, vol. 76, No. 23, pp. 6835-6847 XP002348111.
Pearson P G et al: "Screening strategy for the detection of derivatized glutathione conjugates by tandem mass spectrometry" Analytical Chemistry, American Chemical Society Columbus, US, vol. 62, No. 17, 1990, pp. 1827-1836 XP001203557 ISSN: 0003-2700.
Baillie T A et al: "Mass spectrometry in the analysis of glutathione conjugates" Biological Mass Spectroscopy, Wiley and Sons, Chichester, GB, vol. 22, No. 6, 1993, pp. 319-325 XP001016370 ISSN: 1052-9306.

Borman, S: "Nipping Bad Drugs in the Bud" C & EN, May 17, 2004, pp. 36-39.
Evans D C et al: "Drug-Protein Adducts: An Industry Perspective on Minimizing the Potential for Drug Bioactivation in Drug Discovery and Development" Chem. Res. Toxicol. vol. 17, No. 1, 2004, published on Web Dec. 12, 2003, pp. 3-16.
Gan J et al: Dansyl Glutathione as a Trapping Agent for the Quantitative Estimation and Identification of Reactive Metabolites, Chem. Res. Toxicol. vol. 18, No. 5, 2005, published on the Web Apr. 20, 2005, pp. 896-903.
Vanden Heuvel W J A: "Drug Metabolite Identification: Stable Isotope Methods" J Clin Pharmacol, Jul./Aug. 1986, vol. 26, pp. 427-434.
Samuel K: Addressing the Metabolic Activation Potential of New Leads in Drug Discovery: A Case Study Using Ion Trap Mass Spectrometry and Tritium Labeling Techniques, Journal of Mass Spectrometry, vol. 38, 2003, pp. 211-221.
Pearson P G et al: "Screening Strategy for the Detection of Derivatized Glutathione Conjugates by Tandem Mass Spectrometry" Anal. Chem. vol. 62, 1990, pp. 1827-1836.
Mutlib A et al: "Formation of Unusual Glutamate Conjugates of 1-[3-(Aminomethyl)phenyl]-*N*-[3-Fluoro-2'-(Methylsulfony1)-[1,1'-Biphenyl]-4-YL]-3-(Trifluoromethyl)-1*H*-Pyrazole-5-Carboxamide (DPC 423) and its Analogs: The Roole of γ-Glutamyltranspeptidase in the Biotransformation of Benzylamines", The American Society for Pharmacology and Experimental Therapeutics, vol. 29, No. 10, 2001, pp. 1296-1306.
Mutlib A: "Application of Stable Isotope Labeled Glutathione and Rapid Scanning Mass Spectrometers in Detecting and Characterizing Reactive Metabolites" Rapid Communications in Mass Spectrometry, vol. 19, 2005, pp. 3482-3492.
Baillie T A: "Mass Spectrometry in the Analysis of Glutathione Conjugates", Biological Mass Spectrometry, vol. 22, 1993, pp. 319-325.
Adang A E P: "The Glutathione-Binding Site in Glutathione S-Transferases", Biochem J., vol. 269, 1990, pp. 47-54.
Zhengyin, Yan et al., "Use of Trapping Agent for Simultaneous Capturing and High-Throughput Both "Soft" and "Hard" Reactive Metabolites", Analytical Chemistry, vol. 79, No. 11, 2007, pp. 4206-4214.
Zhengyin, Yan et al., "Rapid Detection and Characterization of Minor Reactive Metabolites Using Stable-Isotope Trapping in Combination with Tandem Mass Spectrometry", Rapid Communications in Mass Spectrometry, vol. 19, No. 22, 2005, pp. 3322-3330.

* cited by examiner

*Primary Examiner*—Cecilia Tsang
*Assistant Examiner*—Thomas S Heard
(74) *Attorney, Agent, or Firm*—Mary A. Appollina

(57) ABSTRACT

The present invention is directed to an isotopically labeled trapping agent, methods for detecting reactive metabolites and methods of identifying drug candidates. More specifically, the isotopically labeled trapping agent and methods for detecting reactive metabolites may be used to detect both "hard" and "soft" reactive metabolites, thereby eliminating false positives.

39 Claims, 20 Drawing Sheets

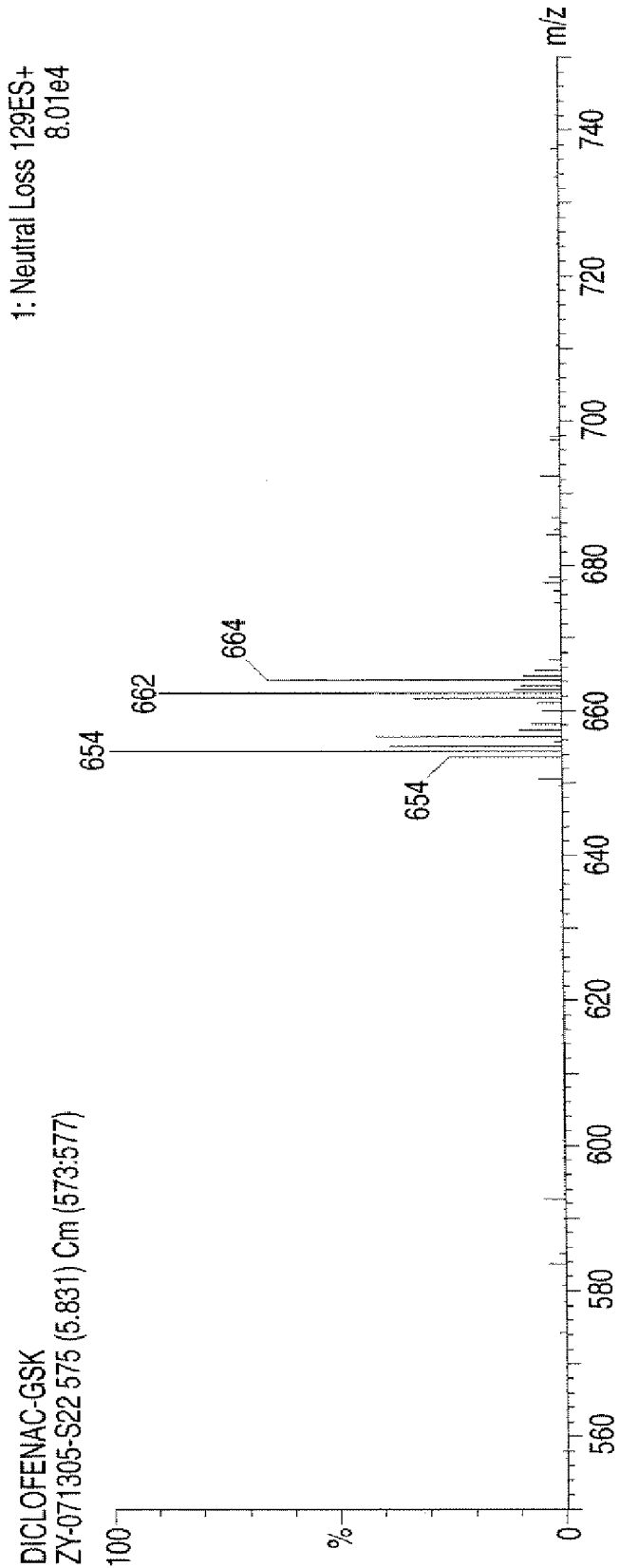

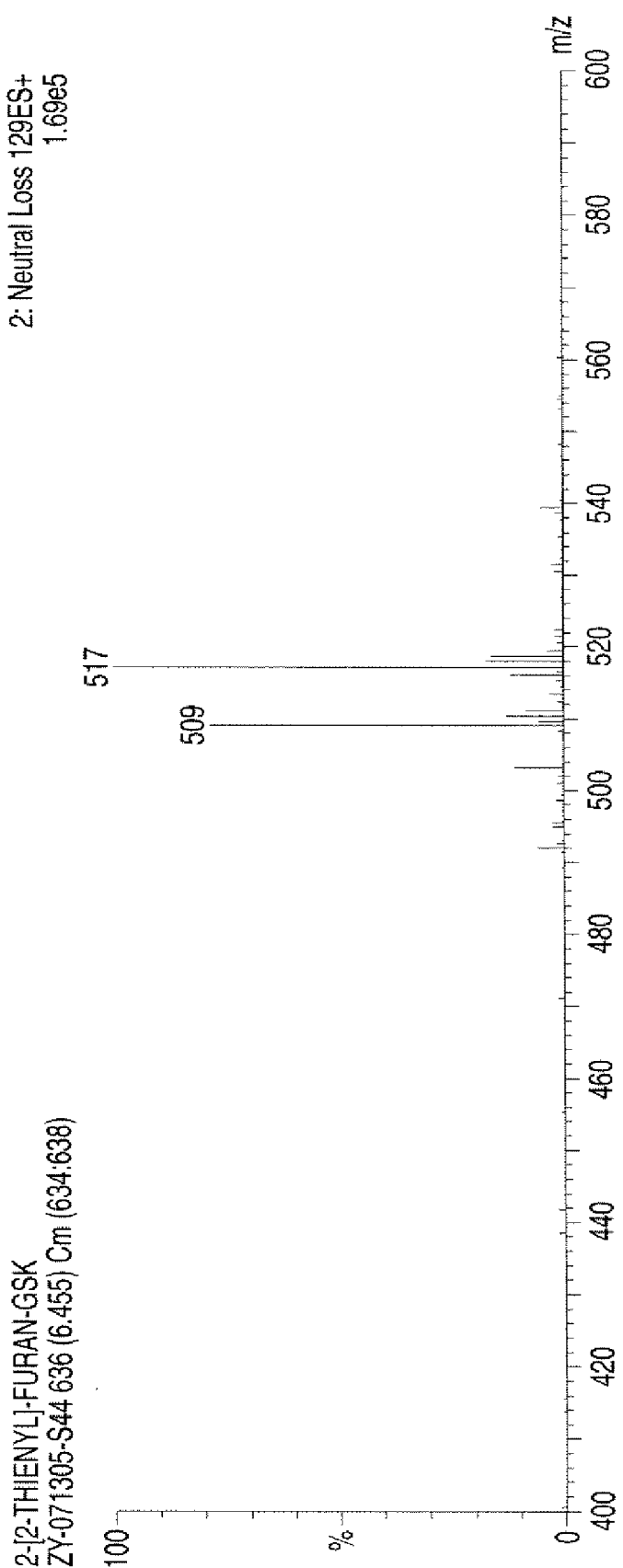

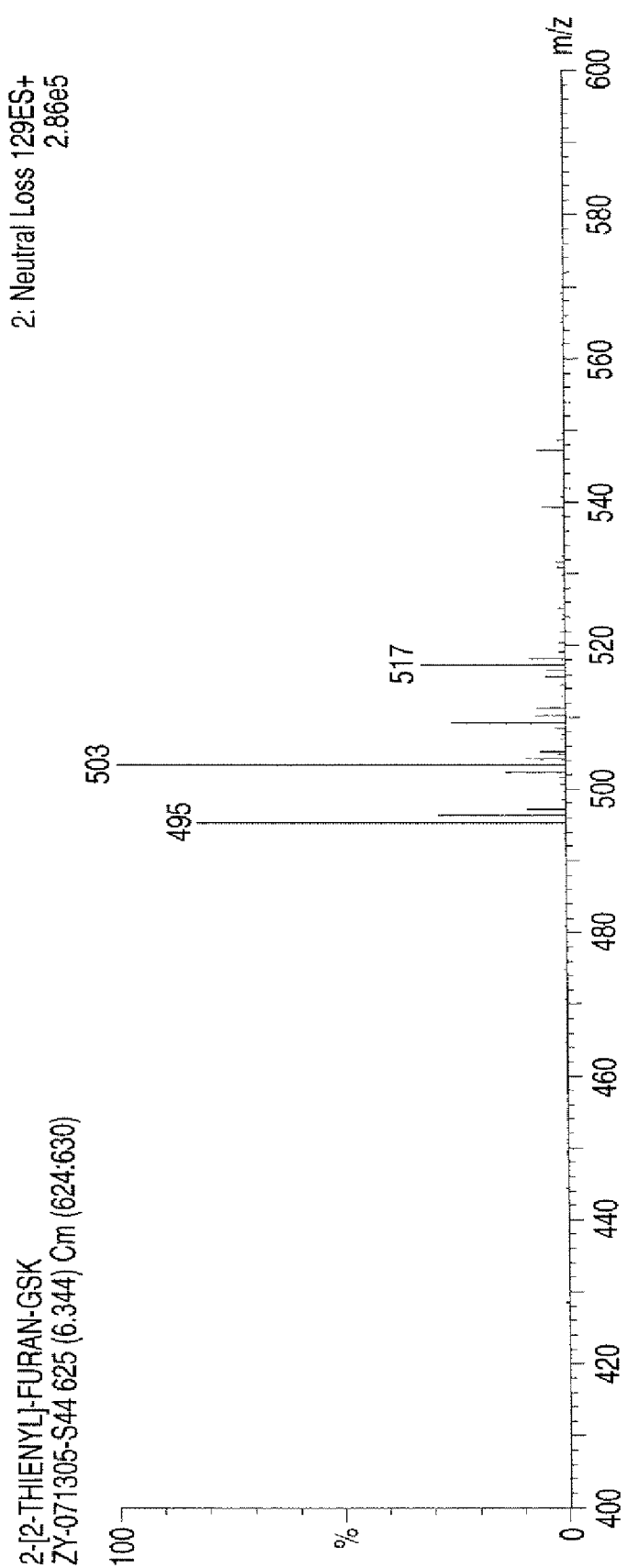

ISOTOPICALLY LABELED TRAPPING AGENT AND METHOD FOR IDENTIFYING REACTIVE METABOLITES

CROSS REFERENCE TO RELATED APPLICATION

This application claims priority from U.S. Provisional Application Ser. No. 60/827,526, filed on Sep. 29, 2006, the contents of which are hereby incorporated by reference in their entirety.

FIELD OF THE INVENTION

The present invention is directed to an isotopically labeled trapping agent, methods for detecting reactive metabolites and methods of identifying drug candidates. More specifically, the isotopically labeled trapping agent and methods for detecting reactive metabolites may be used to detect both "hard" and "soft" reactive metabolites, thereby eliminating false positives.

BACKGROUND OF THE INVENTION

One cause of patient morbidity and mortality, idiosyncratic drug toxicity remains a serious safety concern in both clinical drug development and after market launch. These idiosyncratic drug reactions can lead to restricted use and even withdrawal from the market, which consequently results in higher development cost for the pharmaceutical industry. For example, troglitazone, benoxaprofen and zomepirac were withdrawn from the market shortly after their release due to unacceptable toxicity profiles.

Idiosyncratic drug reactions are a rare event that usually shows in a high degree of individual susceptibility. In addition, these reactions are usually not dose-dependent. Currently, there are no animal models that can be used to evaluate such reactions that exclusively occur in humans. Therefore, idiosyncratic drug toxicities cannot be effectively evaluated in preclinical studies, and are often unnoticed in clinical trials.

At present, the mechanisms of idiosyncratic drug reactions are not well understood. There is a substantial amount of evidence to suggest that chemically reactive metabolites are involved in idiosyncratic toxicities, especially for liver toxicity. All drugs associated with idiosyncratic toxicity form reactive metabolites via various metabolic pathways mediated predominately by cytochrome P450 enzymes (CYPs), as well as by other oxidative enzymes such as peroxidases, cyclooxygenases and myeloperoxidases. It is hypothesized that drugs associated with such toxicities first undergo metabolic activation to generate toxic reactive metabolites that covalently bind to cellular proteins. These covalently modified proteins are immunogenic and thus trigger an immune response, resulting in idiosyncratic drug reactions. An alternative hypothesis states that covalent modifications of cellular proteins by reactive metabolites impair signal transduction cascades and vital functions of cells, leading to severe consequences observed in clinic. Thus there remains a need for methods for identifying reactive metabolites.

Chemically reactive metabolites can be classified into two categories based on their chemical properties—"soft" and "hard" reactive metabolites. "Soft" reactive metabolites comprise a majority of electrophilic metabolites which include quinones, quinone imines, iminoquinone methides, epoxides, arene oxides and nitrenium ions, and readily react with "soft" electrophiles such as the sulfhydryl group in cysteine. In contrast, "hard" reactive metabolites, most commonly seen as aldehydes, preferentially react to "hard" electrophiles such as amines of lysine, arginine and nucleic acids. Because of their instability, direct detection and characterization of reactive metabolites has proven to be extremely difficult. A commonly utilized approach is to trap reactive metabolites with a capture molecule, resulting in formation of a stable adduct that can be subsequently characterized by known detection methods, for example by tandem mass spectrometry.

Recently, Avery, Michael, J., in European Patent Publication EP 1,150,120 disclosed a high-throughput screening method for identifying test compounds producing reactive metabolites. The method comprises incubating a test compound with a microsomal drug metabolizing enzyme system in the presence of glutathione and detecting glutathione adducts formed therefrom using tandem mass spectrometry.

This method however, will identify reactive metabolites as well as non-reactive components, (including both unreactive metabolites and components of the reaction mixture), formed as a result of common response in mass spectroscopy detection, thus resulting in false positives.

Yan et al., in US Patent Publication 2005 0287623 A1 disclose a method for detecting reactive metabolites using stable isotope trapping and mass spectroscopy. However, the method as disclosed in Yan et al., detects only "soft" metabolites, but does not simultaneously detect both "hard" and "soft" reactive metabolites.

SUMMARY OF THE INVENTION

The present invention is directed to an isotopically labeled trapping agent for identifying reactive metabolites, a compound of formula (I)

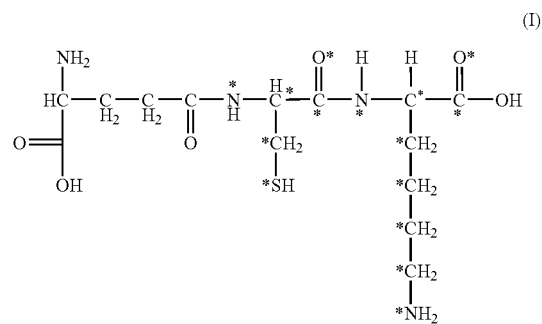

also known as 6-amino-2-[2-(4-amino-4-carboxy-butyrylamino)-3-mercapto-propionylamino]-hexanoic acid, wherein one or more of the carbon, nitrogen, oxygen, sulfur and/or non-exchangeable hydrogen atoms on the starred groups is isotopically labeled.

The present invention is further directed to a method of identifying reactive metabolites comprising (a) incubating a compound of formula (I)

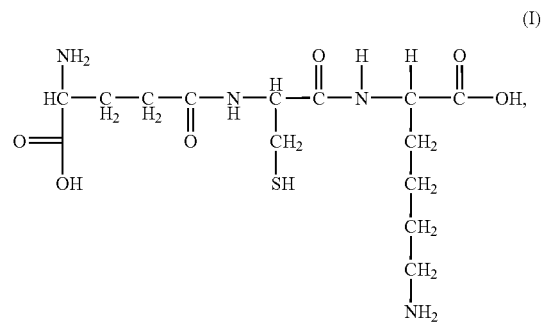

and/or an isotopically-labeled compound of formula (I)

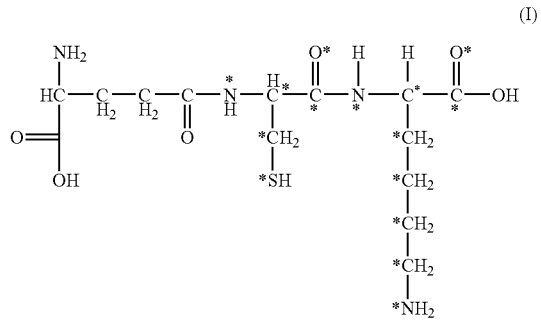

(I)

wherein one or more of the carbon, nitrogen, oxygen, sulfur and/or non-exchangeable hydrogen atoms on the starred groups is isotopically labeled;

with a test compound and a drug metabolizing enzyme;

to yield a product mixture comprising one or more adducts; and (b) detecting said one or more adducts, according to known methods and/or according to the methods as described herein, for example by neutral loss mass spectroscopy.

The present invention is further directed to a method for detecting reactive metabolites of a test compound comprising (a) incubating a test compound with a mixture comprising a compound of formula (I)

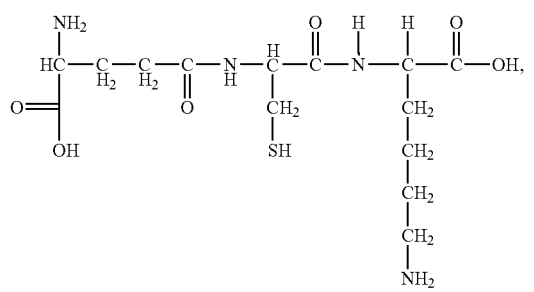

(I)

an isotopically labeled compound of formula (I)

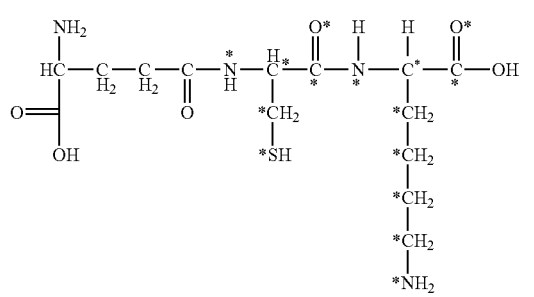

(I)

wherein one or more of the carbon, nitrogen, oxygen, sulfur or non-exchangeable hydrogen atoms on the starred groups is isotopically labeled; and a drug metabolizing enzyme;

to yield a product mixture comprising one or more adducts;

(b) detecting one or more isotopic doublets in a neutral loss mass spectrum of the one or more adducts produced in Step (a), wherein the doublet differs in mass by the difference in mass between the compound of formula (I) and the isotopically labeled compound of formula (I).

The present invention is further directed to a method of identifying reactive metabolites (including both "soft" and/or "hard" reactive metabolites), using a mixture of a compound of formula (I) and an isotopically labeled compound of formula (I), wherein one or more of the carbon, nitrogen, oxygen, sulfur or non-exchangeable hydrogen atoms on the starred groups is isotopically labeled.

The present invention is further directed to a method for detecting reactive metabolites of a test compound comprising (a) incubating a test compound with a mixture comprising a non-isotopically labeled compound of formula (I)

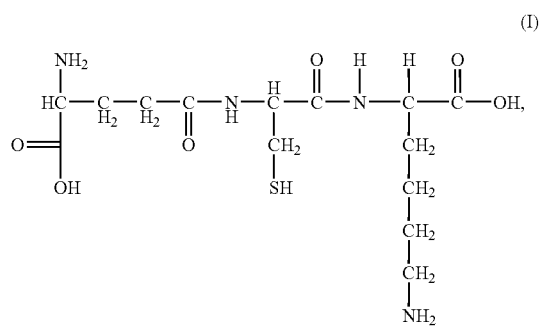

(I)

an isotopically-labeled compound of formula (I)

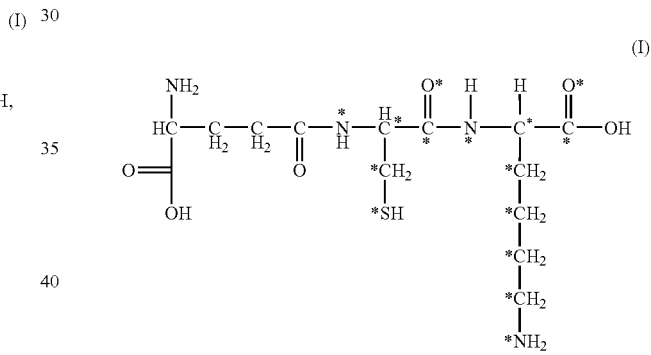

(I)

wherein one or more of the carbon, nitrogen, oxygen, sulfur and/or non-exchangeable hydrogen atoms on the starred groups is isotopically labeled, and a drug metabolizing enzyme, to yield a product mixture comprising one or more adducts;

(b) measuring a neutral loss mass spectrum of the one or more adducts produced in step (a); and (c) detecting one or more isotopic doublets in the neutral loss mass spectrum of step (b), wherein the isotopic doublet(s) differs in mass by the difference in mass between the non-isotopically labeled compound of formula (I) and the isotopically-labeled compound of formula (I).

The present invention is further directed to a mixture comprising (a) a covalently bonded complex of a reactive metabolite and a non-isotopically labeled compound of formula (I) and (b) a covalently bonded complex of a reactive metabolite and an isotopically-labeled compound of formula (I).

The present invention is further directed to a method for identifying a drug candidate comprising (a) incubating a test compound with a non-isotopically labeled compound of formula (I)

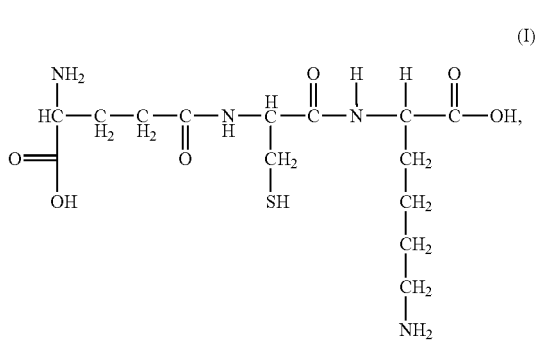

an isotopically-labeled compound of formula (I)

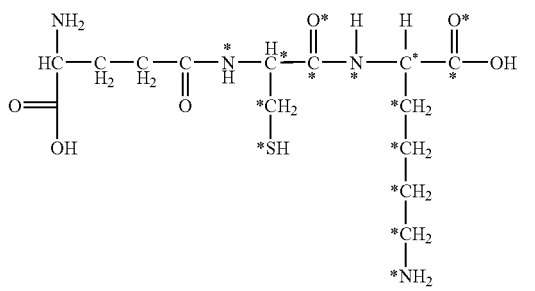

wherein one or more of the carbon, nitrogen, oxygen, sulfur and/or non-exchangeable hydrogen atoms on the starred groups is isotopically labeled, and a drug metabolizing enzyme, to yield a product mixture;

(b) measuring a neutral loss mass spectrum of the product mixture produced in step (a); and (c) detecting the absence of isotopic doublets in the neutral loss mass spectrum of step (b) (wherein the isotopic doublet(s) differs in mass by the difference in mass between the non-isotopically labeled compound of formula (I) and the isotopically-labeled compound of formula (I)).

BRIEF DESCRIPTION OF THE FIGURES

FIG. 1C illustrates the neutral loss tandem mass spectrum of adduct II derived from diclofenac.

FIG. 8B illustrates the neutral loss tandem mass spectrum of adduct I derived from 2-[2-thienyl]-furan.

FIG. 8D illustrates the neutral loss tandem mass spectrum of adduct III derived from 2-[2-thienyl]-furan.

DETAILED DESCRIPTION OF THE INVENTION

Figure 1A:
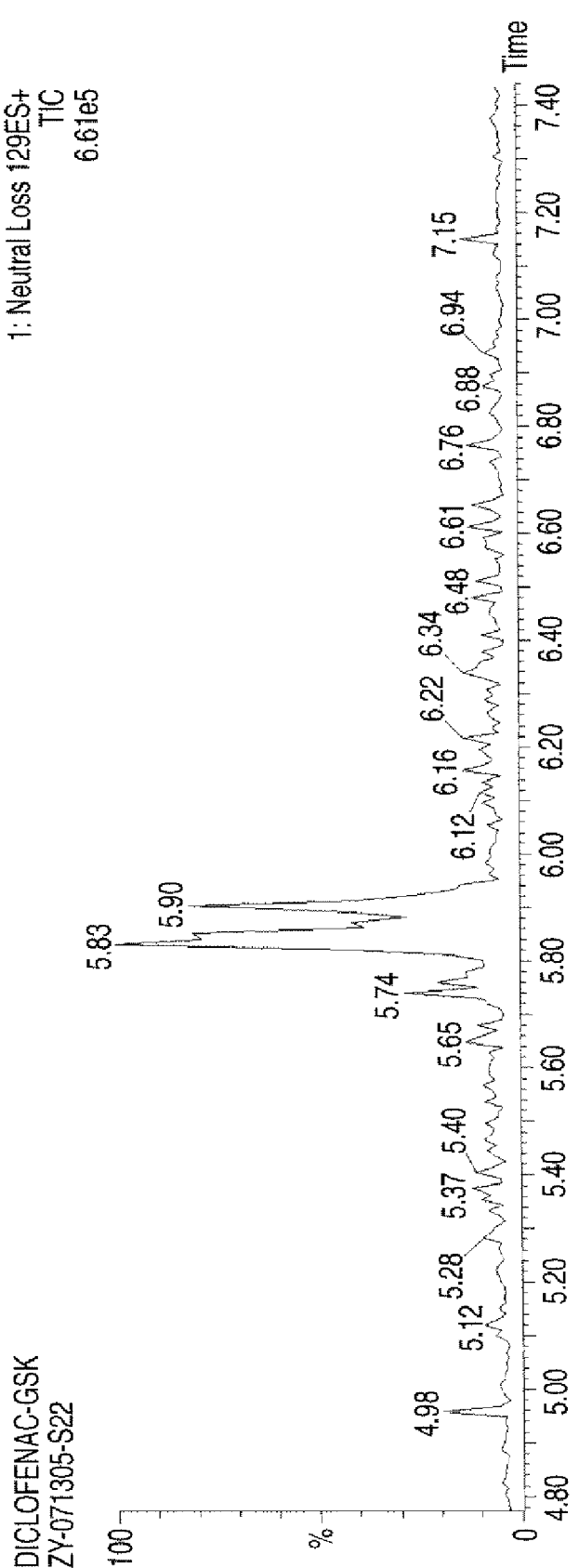
FIG. 1A illustrates the total ion chromatogram of neutral loss scanning of 129 Da for diclofenac.

The present invention is directed to an isotopically labeled trapping agent, wherein the trapping agent is capable of binding to reactive metabolites, a compound of formula (I)

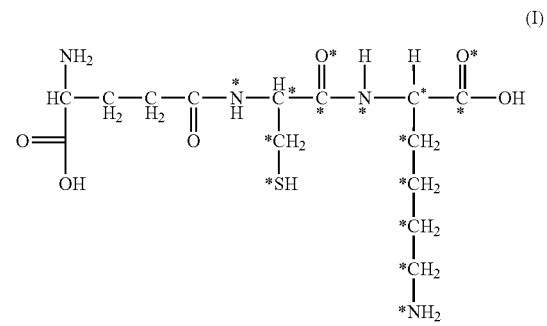

also known as 6-amino-2-[2-(4-amino-4-carboxy-butyrylamino)-3-mercapto-propionylamino]-hexanoic acid, wherein one or more of the carbon, nitrogen, oxygen, sulfur and/or non-exchangeable hydrogen atoms of the starred groups is isotopically labeled, preferably with one or more $^{13}C$, $^{15}N$, $^{18}O$, $^{2}H$ and/or $^{34}S$ isotopes.

As used herein, unless otherwise noted, the term "non-exchangeable hydrogen" shall mean any hydrogen atom which does not exchange in aqueous solution. For the compound of formula (I), the non-exchangeable hydrogen atoms which may be isotopically labeled are designated by the arrows in the structure shown below

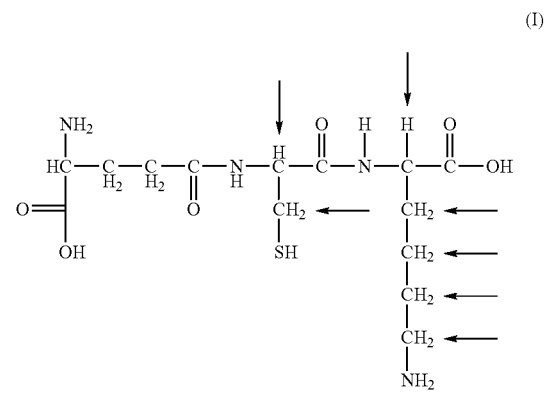

The compound of formula (I) has two "trapping zones", which individually trap "hard" and "soft" reactive metabolites. More specifically, the sulfhydryl (—SH) group on the compound of formula (I) reacts with and traps so-called "soft" reactive metabolites, whereas, the —(CH$_2$)$_4$—NH$_2$ group on the compound of formula (I) reacts with and traps so-called "hard" reactive metabolites. Thus the compound of formula (I) and isotopically labeled compounds of formula (I) are capable of simultaneously trapping both "hard" and "soft" reactive metabolites. This is also shown schematically below.

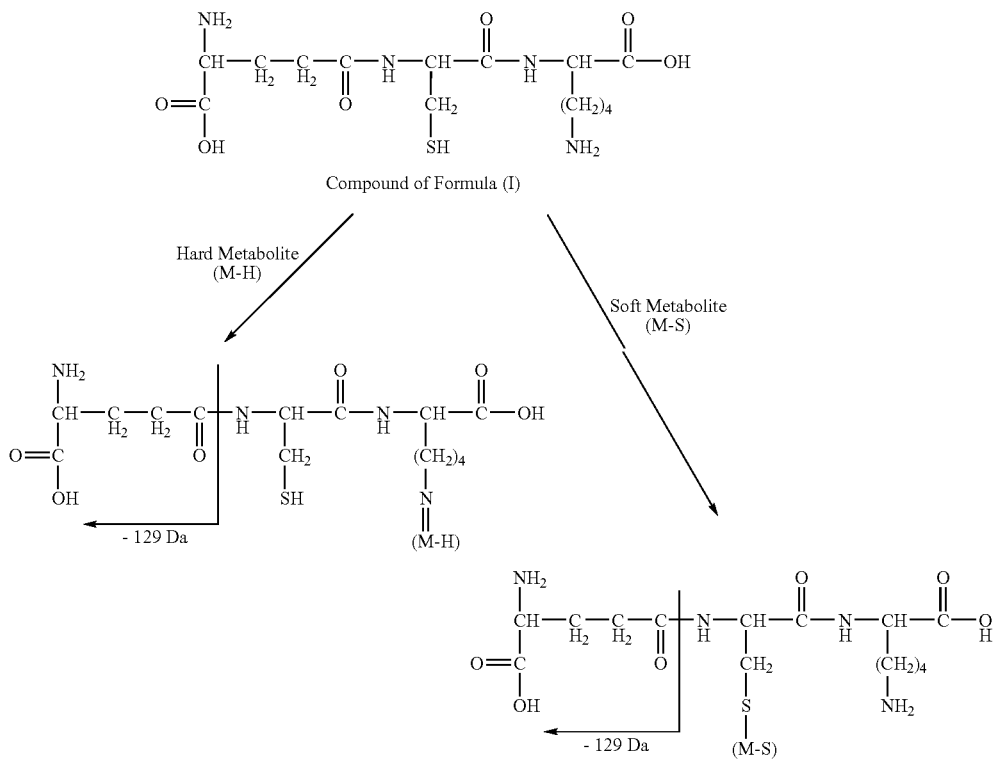

Compound of Formula (I)

Hard Metabolite (M-H)

Soft Metabolite (M-S)

−129 Da (M-H)

−129 Da (M-S)

As used herein, unless otherwise noted, the term "reactive metabolites" shall include "soft" and "hard" reactive metabolites.

As used herein, unless otherwise noted, the term "soft metabolite" shall mean any electrophilic metabolite which comprise at least one substituent group which readily reacts with "soft" electrophiles such as the sulfhydryl group in cysteine and the —SH group on the compound of formula (I). Suitable examples of such substituent groups include, but are not limited to quinones, quinone imines, iminoquinone, methids, epoxides, arene oxides, nitrenium ions, and the like.

As used herein, unless otherwise noted, the term "hard metabolite" shall mean electrophilic metabolite which comprises at least one substituent group which readily reacts with "hard" electrophiles such as the amines of lysine, arginine or the —(CH$_2$)$_4$—NH$_2$ of the compound of formula (I). Suitable examples of such substituent groups include, but are not limited to aldehydes, and the like.

Since reactive metabolites are implicated in many adverse events associated with test compounds, particularly serious and/or toxic adverse events, it is highly desirable to be able to detect all reactive metabolites produced by a test compound. It is further highly desirable to determine whether a test compound will produce reactive metabolites prior to administration of the test compound to humans.

One skilled in the art will recognize that not all test compounds produce reactive metabolites and further, that not all test compounds produce both "soft" and "hard" reactive metabolites. Some test compounds will produce no reactive metabolites, some test compounds will produce only hard reactive metabolites, some test compounds will produce only soft reactive metabolites, and some test compounds will produce both hard and soft reactive metabolites. Thus the trapping agent and methods of the present invention will detect any type of reactive metabolite that is produced by a test compound.

One skilled in the art will further recognize that the methods of the present invention, while directed to identifying reactive metabolites, also encompass the process of determining whether or not a test compound produces reactive metabolites. In an embodiment, the present invention is directed to a method for identifying drug candidates (e.g. test compounds which do not produce reactive metabolites). Thus, the methods of the present invention include processes wherein the incubation (as described in more detail herein) results in no reactive metabolites and thus no adducts, and the mass spectra show no doublets, thereby indicating that the test compound does not produce any detectable reactive metabolites.

For "soft" metabolites, glutathione, a compound of following chemical structure

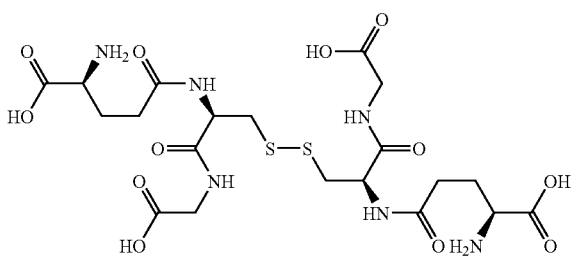

is the most common trapping agent used in microsomal incubations, for detecting "soft" reactive metabolites. However, for "hard" reactive metabolites, glutathione is not a suitable trapping agent because of its low trapping efficiency. Rather, for detecting "hard" reactive metabolites alternative trapping agents such as semicarbazide, methoxylamine and α-acetyllisine are used. This requires two individual experiments with different trapping agents for the detection of both "hard" and "soft" reactive metabolites. In contrast, the compound of formula (I), isotopically labeled compounds of formula (I) and/or a mixture of non-isotopically labeled compound of formula (I) and isotopically labeled compound of formula (I) may be used to detect both "soft" and "hard" reactive metabolites in a single experiment.

As used herein, unless otherwise noted, the term "isotopically-labeled compound of formula (I)" shall mean a compound of formula (I) which is labeled with at least one isotope, for example, $^{13}C$, $^{15}N$, $^{18}O$, $^{2}H$, $^{3}H$, $^{34}S$, and the like. Preferably, the isotope is $^{13}C$, $^{15}N$, $^{18}O$ or $^{2}H$. Suitable examples of isotopically-labeled compound of formula (I) include, but are not limited to compounds of formula (I) labeled with $^{13}C$ and/or $^{15}N$ at its cysteine; compounds of formula (I) isotopically labeled at both its cysteine and lysine groups; compounds of formula (I) labeled at single or multiple position(s) ranging from 1 to 28, preferably 1 to 10 positions, more preferably 3 to 8 positions, most preferably 8 positions; and the like. Preferably, the isotopically-labeled compound of formula (I) is labeled with at least one isotope selected from the group consisting of $^{13}C$, $^{15}N$, $^{18}O$ and $^{2}H$. More preferably, the isotopically labeled compound of formula (I) is labeled with two $^{15}N$ and six $^{13}C$ isotopes.

In an embodiment, the isotopically labeled compound of formula (I) is isotopically labeled as indicated in the chemical structure (I-IS) shown below

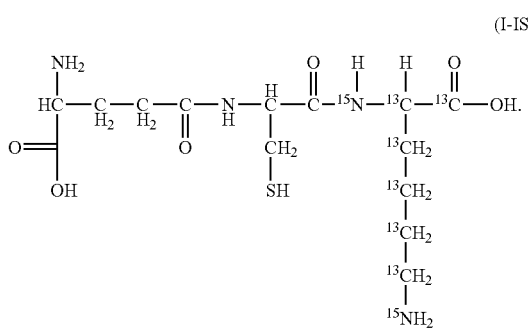

(I-IS)

As used herein, unless otherwise noted "drug metabolizing enzyme" shall mean any enzyme or mixture thereof, derived from human or animal tissues, preferably derived from human tissues, more preferably derived from human liver tissue, which can metabolize a test compound. (See for example, *Drug Metabolizing Enzymes*, Edited by Jae S. Lee, R. Scott Obach and Michael B. Fisher, Marcel Dekker, Inc. (2003)) Suitable examples include, but are not limited to liver microsomes, cytochrome P450 enzymes or mixtures of different isoforms of cytochrome P450 enzymes, peroxidases, cyclooxygenases, myeloperoxidases, and the like. Preferably, the drug metabolite enzymes are human liver microsomes, more preferably, cytochrome P450 enzymes. One skilled in the art will recognize that when incubating a test compound with cytochrome P450 enzymes or mixtures of different isoforms of cytochrome P450 enzymes, the cytochrome P450 enzymes or mixtures of different isoforms of cytochrome P450 enzymes are incubated in combination with NADPH co-factor or the NADPH regenerating system.

As used herein, unless otherwise noted, the term "test compound" shall mean any chemical which is tested for the formation of reactive metabolite(s). Preferably, the test compound is a pharmaceutical agent or salt, ester or pro-drug thereof.

As used herein, unless otherwise noted, the term "drug candidate" shall mean any chemical or test compound which does not produce reactive metabolite(s). Preferably, the drug candidate is a pharmaceutical agent or salt, ester or pro-drug thereof.

As used herein, unless otherwise indicated, the term "adduct" shall mean any covalently bonded complex of a reactive metabolite with an isotopically labeled compound of formula (I) or with a non-isotopically labeled compound of formula (I).

Abbreviations used in the specification, particularly the Schemes and Examples, are as follows:
APCI-MS/MS=Atmospheric pressure chemical ionization tandem mass spectrometry
CYPs=Cytochrome P450 enzymes
Da=Daltons
ESI-MS/MS=Electrospray ionization tandem mass spectrometry
HPLC=High pressure liquid chromatography
MS=Mass Spectroscopy
NADPH=β-nicotinamide adenine dinucleotide phosphate (reduced)
SPE Solid phase extraction In an embodiment, the present invention is directed to an isotopically labeled compound of formula (I) wherein one or more of the carbon, nitrogen, oxygen, sulfur and/or non-exchangeable hydrogen atoms of the starred groups is isotopically labeled, preferably with one or more $^{13}C$, $^{15}N$, $^{18}O$, $^{2}H$, $^{3}H$ and/or $^{34}S$ isotopes. The isotopically labeled compound of formula (I) may be prepared according to known methods, for example by isotope exchange or by peptide coupling synthesis using an isotopically labeled reagent/starting material. (See for example, Ott, Donald G., Syntheses with Stable Isotopes of Carbon, Nitrogen, and Oxygen, (1981), Wiley, New York, N.Y.; Keliher, Edmund J.; Burrell, Richard C.; Chobanian, Harry R.; Conkrite, Karina L.; Shukla, Rajesh; Baldwin, John E., Efficient syntheses of four stable—isotope labeled (1R)-menthyl (1S,2S)-(+)-2-phenylcyclopropanecarboxylates, Organic & Biomolecular Chemistry, (2006), 4(14), pp 2777-2784; Schippers, Nicole; Schwack, Wolfgang, Synthesis of the 15N-labelled insecticide imidacloprid, Journal of Labelled Compounds and Radiopharmaceuticals, (2006), 49(3), pp 305-310; and Bretz, Michael; Beyer, Marita; Cramer, Benedikt; Humpf, Hans-Ulrich, Synthesis of stable isotope labeled 3-acetyldeoxynivalenol, Molecular Nutrition & Food Research, (2005), 49(12), pp 1151-1153.)

In an embodiment, the present invention is directed to an isotopically labeled compound of formula (I-IS). The compound of formula (I-IS) may be prepared as outlined in Scheme 1 below.

Scheme 1

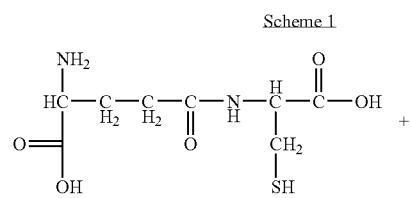

-continued

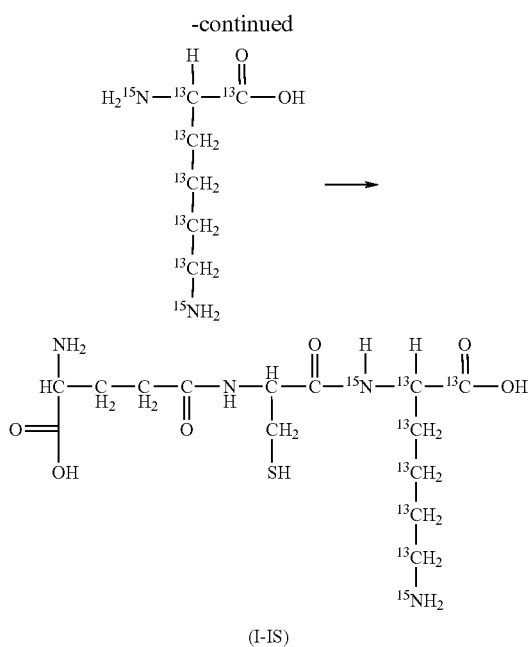

(I-IS)

Accordingly, 2-amino-4-(1-carboxy-2-mercapto-ethylcarbamoyl)-butyric acid is reacted with isotopically labeled lysine, according to known chemistry (for example via acid-amine condensation with the loss of water; see for example Wade, L. G., *Organic Chemistry*, Fourth Editions, Prentice Hall, 1999, pp. 136-137), to yield the compound of formula (I-IS).

The present invention is directed to the use of a compound of formula (I)

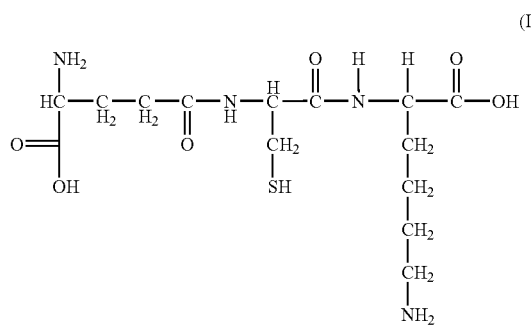

or an isotopically labeled compound of formula (I)

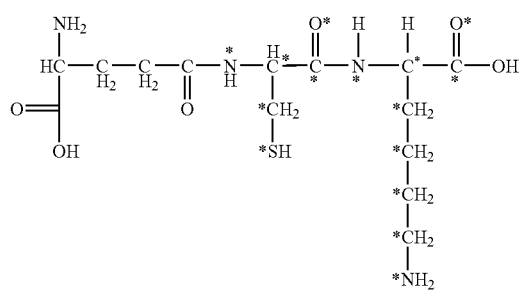

wherein one or more of the carbon, nitrogen, oxygen, sulfur or non-exchangeable hydrogen atoms on the starred groups is isotopically labeled;

or a mixture of a compound of formula (I) and an isotopically labeled compound of formula (I);

for detecting reactive metabolites.

The present invention is further directed to a method for detecting reactive metabolites using isotope trapping and mass spectroscopy, wherein the method eliminates false positives. The present invention further provides a highly sensitive method for detecting reactive metabolites at low levels. Additionally, the present invention may be applied to the detection of reactive metabolites in a manual or in a fully automated manner using MS pattern recognition.

The present invention is further directed to a method for detecting reactive metabolites comprising (a) incubating a compound of formula (I) or an isotopically-labeled compound of formula (I), wherein one or more of the carbon, nitrogen, oxygen, sulfur and/or non-exchangeable hydrogen atoms on the starred groups is isotopically labeled, with a test compound and a drug metabolizing enzyme to produce a product mixture comprising one or more adducts; and (b) detecting said adducts (according to known methods).

For example, a method for detecting reactive metabolites without stable isotope trapping (e.g. without the use of an isotopically labeled trapping agent, such as an isotopically labeled compound of formula (I)) employs a triple quadrupole mass spectrometer that can trigger MS/MS full scan by using neutral loss as a survey scan. Using this system, tandem MS spectra of the adducts can be obtained in a single run, and structural identification can be achieved by examining characteristic product ions. However, because of the smaller signal to noise ratio typically achieved with MS full scans relative to neutral loss MS scans, it may be difficult to detect minor reactive metabolite using the MS full scan systems. Further, MS full scans are relatively time and labor intensive.

The present invention is directed to a method for detecting reactive metabolites of a test compound comprising (a) incubating a test compound with a mixture comprising a non-isotopically labeled compound of formula (I), an isotopically labeled compound of formula (I), wherein one or more of the carbon, nitrogen, oxygen, sulfur and/or non-exchangeable hydrogen atoms on the starred groups is isotopically labeled, and a drug metabolizing enzyme to yield a product mixture comprising one or more adducts;

(b) detecting one or more isotopic doublets in a neutral loss mass spectrum of the adducts of step (a), wherein the doublet differs in mass by the difference in mass between the non-isotopically labeled compound of formula (I) and the isotopically-labeled compound of formula (I).

In an embodiment, the present invention is directed to a method for detecting reactive metabolites of a test compound comprising (a) incubating a test compound with a mixture comprising a compound of formula (I),

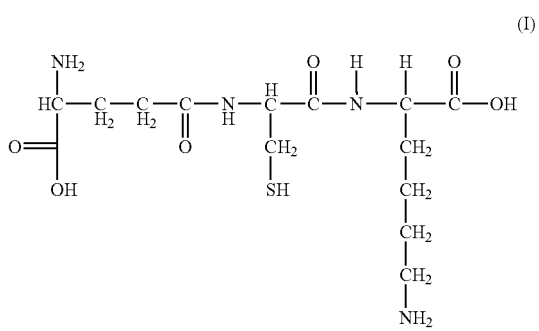

(I)

an isotopically-labeled compound of formula (I-IS)

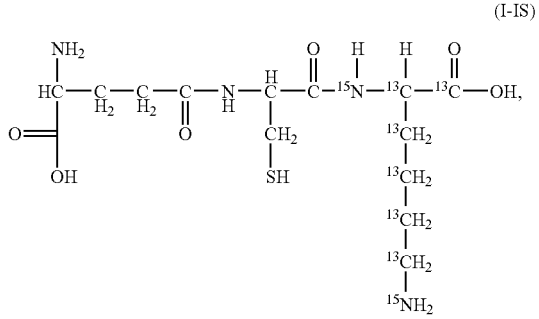

(I-IS)

and a drug metabolizing enzyme;

to yield a product mixture comprising one or more adducts;

(b) measuring a neutral loss mass spectrum of the one or more adducts produced in step (a); and (c) detecting one or more isotopic doublets in the neutral loss mass spectrum of step (b), wherein the isotopic doublets differ in mass by 8 Da.

In an embodiment, the present invention is directed to a method for detecting reactive metabolites of a test compound comprising (a) incubating a test compound with a mixture comprising a non-isotopically labeled compound of formula (I), an isotopically labeled compound of formula (I), wherein one or more of the carbon, nitrogen, oxygen, sulfur and/or non-exchangeable hydrogen atoms on the starred groups is isotopically labeled, and a drug metabolizing enzyme to yield a product mixture comprising one or more adducts;

(b) separating the one or more adducts of step (a); (according to known methods, preferably, by centrifuge)

(c) measuring a neutral loss mass spectrum of said separated adducts;

(d) detecting one or more isotopic doublets in the neutral loss mass spectrum of said separated adducts, wherein the doublet differs in mass by the difference in mass between the non-isotopically labeled compound of formula (I) and the isotopically labeled compound of formula (I).

In an embodiment, the present invention is directed to a method for detecting reactive metabolites of a test compound comprising Step A: incubating a mixture comprising
(a) a test compound;
(b) a compound of formula (I)

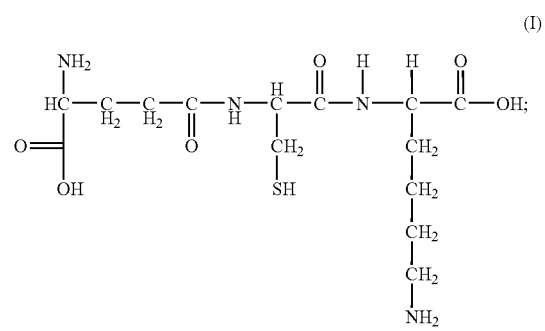

(I)

(c) an isotopically labeled compound of formula (I-IS)

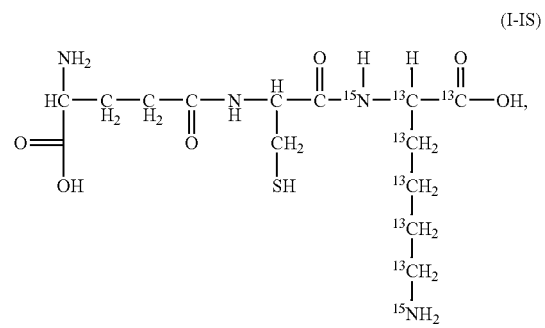

(I-IS)

wherein the molar ratio of the compound of formula (I) to the isotopically labeled compound of formula (I-IS) is about 1:1; and (c) a drug metabolizing enzyme selected from the group consisting of human liver microsomes, cytochrome P450 enzymes in combination with NADPH co-factor and cytochrome P450 enzymes in combination with NADPH regenerating system;

to yield a product mixture comprising one or more incubation products selected from the group consisting of (a) a non-reactive metabolite;

(b) an adduct formed between the compound of formula (I) and a reactive metabolite; and (c) an adduct formed between the isotopically labeled compound of formula (I-IS) and a reactive metabolite;

Step B: measuring a neutral loss mass spectrum of the product mixture produced in Step (A); and Step C: detecting one or more isotopic doublets in the neutral loss mass spectrum of Step (B), wherein the isotopic doublets differ in mass by 8 Da.

In an embodiment of the present invention, the isotopically labeled compound of formula (I) is labeled with at least one isotope selected from the group consisting of $^{13}C$, $^{15}N$, $^{18}O$ and $^{2}H$. In another embodiment of the present invention, the isotopically labeled compound of formula (I) is labeled with 1 to 28 isotopes, preferably 1 to 10 isotopes. In another embodiment of the present invention, the isotopically labeled compound of formula (I) is labeled with six $^{13}C$ and two $^{15}N$ atoms. In another embodiment of the present invention, the isotopically labeled compound of formula (I) is the compound of formula (I-IS)

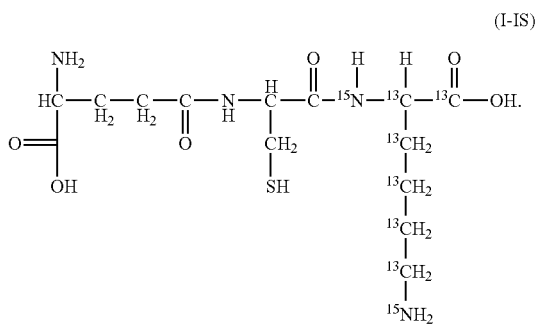
(I-IS)

In an embodiment of the present invention, the neutral loss mass spectrum is used to detect loss of 129 Da (corresponding to the loss of the —C(O)—CH$_2$—CH$_2$—CH(NH$_2$)—CO$_2$H portion of the non-isotopically labeled or isotopically labeled compound of formula (I)).

In an embodiment of the present invention, the isotopic doublet(s) are detected following APCI-MS/MS, ESI-MS/MS, and the like; preferably ESI-MS/MS. In another embodiment of the present invention, the isotopic doublet(s) in the neutral loss mass spectrum differs by a mass of between 1 and 28 mass units, preferably between 2 and 10 mass units, more preferably by 8 mass units.

In an embodiment of the present invention, the drug metabolizing enzyme is selected from the group consisting of human liver microsomes, cytochrome P450 enzymes, peroxidases, cyclooxygenases and myeloperoxidases. Preferably, the drug metabolizing enzyme is cytochrome P450 enzymes.

In an embodiment, the present invention is applied to detecting reactive metabolites formed by incubating a test compound with any fraction of cells containing drug metabolizing enzymes, for example, S9, recombinant enzymes or microsomal enzymes. In an embodiment, the methods of the present invention are applied to predicting whether or not a test compound will form reactive metabolites in human subjects (i.e. following administration of the test compound to a human).

One skilled in the art will understand that the abbreviation "S9" refers to the S9 fraction (post-mitochondrial supernatant fraction) which is a mixture of microsomes and cytosol. Accordingly, it contains a wide variety of phase I and phase II enzymes including P450 enzymes, flavin-monooxygenases, carboxylesterases, epoxide hydrolase, UDP-glucuronosyl-transferases, sulfotransferases, methyltransferases, acetyltransferases, glutath ione S-transferases and other drug-metabolizing enzymes.

The present invention is further directed to a mixture comprising (a) a covalently bonded complex of a reactive metabolite and non-isotopically labeled compound of formula (I) and (b) a covalently bonded complex of a reactive metabolite and isotopically labeled compound of formula (I), wherein one or more of the carbon, nitrogen, oxygen, sulfur and/or non-exchangeable hydrogen atoms on the starred groups is isotopically labeled.

In an embodiment of the present invention, the molar ratio of the non-isotopically labeled compound of formula (I) and the isotopically labeled compound of formula (I) is in the range of from about 1:1 to about 1:2, preferably in the range of from about 1:1 to about 1:1.5, more preferably about 1:1.

In an embodiment of the present invention, the molar ratio of the covalently bonded complex of a reactive metabolite and non-isotopically labeled compound of formula (I) and the covalently bonded complex of a reactive metabolite and isotopically labeled compound of formula (I) is in the range of from about 1:1 to about 1:2, preferably in the range of from about 1:1 to about 1:1.5, more preferably about 1:1.

The present invention is further directed to a method for detecting reactive metabolites. More specifically, in the method of the present invention, a test compound is incubated with a mixture comprising (a) a non-isotopically labeled compound of formula (I);

(b) an isotopically labeled compound of formula (I), wherein the isotopically labeled compound of formula (I) contains six $^{13}$C and two $^{15}$N atoms;

wherein the molar ratio of non-isotopically labeled compound of formula (I) to isotopically labeled compound of formula (I) is about 1:1 (to yield doublets in the mass spectrum which have about the same intensity); and (c) a drug metabolizing enzyme such as, human liver microsomes, cytochrome P450 enzymes (CYPs) (purified, recombinant, in microsomes, in hepatic cells, and the like) in combination with NADPH co-factor, cytochrome P450 enzymes (CYPs) (purified, recombinant, in microsomes, in hepatic cells, and the like) in combination with NADPH regenerating system, peroxidases, cyclooxygenases, myeloperoxidases, and the like; preferably human liver microsomes;

according to known methods;

to yield a product mixture comprising one or more incubation products selected from the group consisting of (a) a non-reactive metabolite;

(b) an adduct formed between a non-isotopically labeled compound of formula (I) and a reactive metabolite; and (c) an adduct formed between an isotopically labeled compound of formula (I) and a reactive metabolite.

One skilled in the art will recognize that non-reactive (stable) metabolites, produced as a result of the above described incubation, will not react with either the non-isotopically labeled compound of formula (I) or the isotopically labeled compound of formula (I), but rather will remain in the product mixture unaltered.

Preferably, the isotopically labeled compound of formula (I) is labeled with one or more isotopes which are selected to be stable. Suitable isotopes include, but are not limited to, $^{13}$C, $^{15}$N, $^{2}$H, $^{3}$H, $^{18}$O, $^{34}$S, and the like. Preferably, the isotopes are selected from the group consisting of $^{13}$C, $^{15}$N, $^{18}$O and $^{2}$H, more preferably $^{13}$C and $^{15}$N. Preferably, the isotopically labeled compound of formula (I) differs in mass from the non-isotopically labeled compound of formula (I) by between 1 and 28 mass units, more preferably between 2 and 10 mass units, most preferably 8 mass units.

The product mixture containing one or more of the incubation products (non-reactive metabolite(s), adducts formed between reactive metabolite(s) and the non-isotopically labeled compound of formula (I) and/or adducts formed between reactive metabolite(s) and the isotopically labeled compound of formula (I)) is preferably cleaned and concentrated according to known methods, for example by centrifuge, SPE or liquid-liquid extractions, to yield a product concentrate. The product concentrate is then dissolved in a solvent suitable for use in mass spectroscopy (i.e. suitable for injection into a mass spectrometer), for example, 5% acetonitrile in water, 5% methanol in water, and the like.

Preferably, the product mixture is separated into individual adduct components according to known methods, for example by liquid chromatography, HPLC, capillary electrophoresis, or other separation technique. A neutral loss mass spectrum is then measured for each adduct or adduct component. The neutral loss mass spectrum may be measured according to known methods, using any ionization source, for example by APCI-MS/MS, ESI-MS/MS, and the like, preferably by ESI-MS/MS. Alternatively, the separation and mass spectrum measurement may be completed in one step using a loop system such as, LC/MS, and the like.

If reactive metabolites are produced from the test compound and are present (as adducts with the non-isotopically labeled compound of formula (I) and isotopically-labeled compound of formula (I)), the corresponding mass spectrum will exhibit one or more doublets spaced by the difference in mass between the non-isotopically labeled compound of formula (I) and the isotopically labeled compound of formula (I). One skilled in the art will recognize that the doublet(s) may be identified either by visual recognition or by using a computer software program which evaluates MS patterns.

As an example, wherein the isotopically-labeled compound of formula (I) is labeled with six $^{13}$C and two $^{15}$N atoms, as in the compound of formula (I-IS), and the non-isotopically labeled compound of formula (I) and the isotopically labeled compound of formula (I) are present at a molar ratio of preferably about 1:1, in collision-induced dissociation, both the non-isotopically labeled and isotopically labeled adducts will undergo a neutral loss of pyroglutamate (129 Da). As a result, the mass spectrum of the adducts formed between reactive metabolites and the non-isotopically labeled compound of formula (I) and isotopically labeled compound of formula (I) will exhibit two isotopic molecular ions that differ in mass by 8 Da, and the isotopic doublet will show approximately equal intensities. A consistent mass difference of 8 Da and approximately equal intensity of said doublet peaks would thereby provide a unique MS signature which would identify the reactive metabolite adduct.

In the processes of the present invention, false positives are readily eliminated since they do not exhibit a characteristic doublet in the measured neutral loss mass spectrum.

Automation of the methods of the present invention may be accomplished, for example, by using computer-assisted MS pattern recognition. As an example, a logical diagram was devised to program a computer to perform automatic detection of reactive metabolites. More specifically, the pattern recognition process consisted of the following steps:

1. defining the error tolerance for the m/z value;
2. defining the error range of peak intensity ratio for a potential isotope doublet;
3. determining chromatographic peaks in the total ion chromatogram with a selected noise-to-signal setting;
4. detecting m/z values of major molecular ions of individual chromatographic peaks;
5. searching for doublets that differed in mass by the appropriate number of Daltons (based on the selected isotope types and number) using defined the error tolerance;
6. determining the intensity ratios of identified doublets;
7. identifying the adducts.

In using this approach, the intensity ratio and the mass difference of the doublet(s) are the most determining parameters in pattern recognition. Error ranges of the intensity ratio are determined by the purity of non-isotopically labeled compound of formula (I) and the isotopically labeled compound of formula (I), while the error tolerance of m/z values is dependent on the performance of mass spectrometers.

The methods of the present invention are intended for determining whether a test compound will produce "hard" and/or "soft" reactive metabolites, in a single experiment. One skilled in the art will recognize that although the methods of the present invention will simultaneously detect both "hard" and "soft" reactive metabolites, if either "hard" or "soft" reactive metabolites are not formed from a particular test compound, the method will detect whichever type of reactive metabolite is formed. Additionally, if no reactive metabolites are formed, the method will produce a mass spectrum without the characteristic doublets, thereby identifying the test compound as a drug candidate.

The present invention is further directed to a method for identifying a drug candidate (i.e. a test compound which does not produce reactive metabolites) comprising (a) incubating a test compound with a mixture comprising a non-isotopically labeled compound of formula (I), an isotopically-labeled compound of formula (I), wherein one or more of the carbon, nitrogen, oxygen, sulfur and/or non-exchangeable hydrogen atoms on the starred groups is isotopically labeled, and a drug metabolizing enzyme, to yield a product mixture;

(b) measuring a neutral loss mass spectrum of the product mixture produced in step (a); and (c) detecting the absence of isotopic doublets in the neutral loss mass spectrum of step (b) (wherein the isotopic doublet(s) differs in mass by the difference in mass between the non-isotopically labeled compound of formula (I) and the isotopically-labeled compound of formula (I)).

In an embodiment, the present invention is directed to a method for identifying a drug candidate comprising (a) incubating a test compound with a mixture comprising a non-isotopically labeled compound of formula (I)

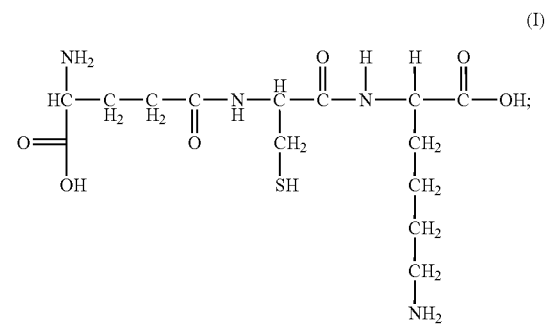

an isotopically labeled compound of formula (I-IS)

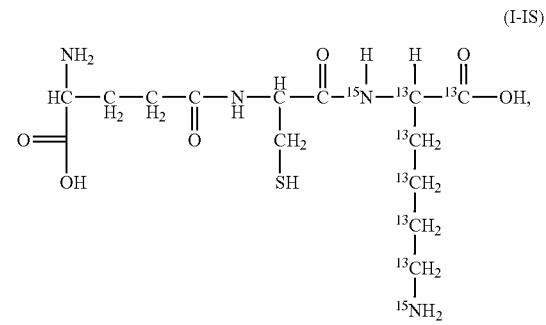

wherein one or more of the carbon, nitrogen, oxygen, sulfur or non-exchangeable hydrogen atoms on the starred groups is isotopically labeled;

and a drug metabolizing enzyme; to yield a product mixture;

(b) measuring a neutral loss mass spectrum of the product mixture produced in Step (a); and (c) detecting the absence of isotopic doublets in the neutral loss mass spectrum of Step (b) (wherein the isotopic doublet(s) differs in mass by the difference in mass by 8 Da).

The following Examples are set forth to aid in the understanding of the invention, and are not intended and should not be construed to limit in any way the invention set forth in the claims which follow thereafter.

EXAMPLE 1

Standard Procedures

A. Incubation & Stable Isotope Trapping:

All microsomal incubations described herein were performed at 37° C. in a water bath. The test compound was mixed with human liver microsomal preparations (cytochrome P450 enzyme preparations) in 50 mM potassium phosphate buffer (pH 7.4) supplemented with the non-isotopically labeled compound of formula (I) and the isotopically labeled compound of formula (I-S) that were pre-mixed at an equal molar ratio of 1:1. The resulting mixtures were pre-warmed at 37° C. for 5 min. To the reaction mixtures was then added the co-factor—NADPH generating system—(to initiate the reaction) to yield a final volume of 1000 µl.

The resulting reaction mixtures contained 10 µM test compounds, 1 mg/ml microsomal proteins, 1 mM mixture of non-isotopically labeled compound of formula (I) and isotopically labeled compound of formula (I-IS), 1.3 mM NADP$^+$, 3.3 mM glucose-6-phosphate, 0.4 U/ml glucose-6-phosphate dehydrogenase, 3.3 mM magnesium chloride.

After a 60 min incubation, the reactions were terminated by the addition of 150 µl of trichloroacetic acid (10%). The resulting mixtures were centrifuged at 10,000 g for 15 min at 4° C. to pellet the precipitated protein, and the supernatants were subjected to solid-phase extractions. Alternatively, the reaction mixtures were subjected to liquid-liquid extractions to recover the metabolites from supernatants.

B. Mass Spectrometry:

MS analyses were performed on a Micromass (Manchester, UK) *Quattro Micro* triple quadrupole mass spectrometer. The ESI ion source was operated in the positive ion mode, and experimental parameters were set as follows: capillary voltage 3.2 kV, source temperature 120° C., desolvation temperature 300° C., sample cone voltage 26 V. Mass spectra collected in the neutral loss scanning mode were obtained by scanning over the range m/z 400-800 in 2.0 s.

C. LC-MS/MS analyses:

For complete profiling of reactive metabolites, samples were first subjected to chromatographic separations with an Agilent 1100 HPLC system with an auto-sampler (Agilent Technologies, Palo Alto, Calif.), and eluents were introduced to the *Quattro Micro* triple quadrupole mass spectrometer operated in the neutral loss scanning mode. An Agilent Zorbax SB C18 column (2.1×50 mm) was used for the chromatographic separation. The starting mobile phase consisted of 95% water (0.5% acetic acid), and the metabolites were eluted using a single gradient of 95% water to 95% acetonitrile over 7 min at a flow rate of 0.3 ml/min. At 7 min, the column was flushed with 95% acetonitrile for 2 min before re-equilibration at initial conditions. LC-MS/MS analyses were carried out on 10-µl aliquots of cleaned samples. Data were processed using the Masslynx version 4.0 software from Micromass. After a positive peak was detected, MS/MS spectra were subsequently obtained to further confirm the structure of the adduct(s). To acquire CID (Collision Induced Dissociation) spectra, the mass spectrometer was operated in the multiple reaction monitoring (MRM) mode.

EXAMPLE 2-9

Detecting Soft and/or Hard Reactive Metabolites

Following the procedure as outlined in Example 1 above, the method of the present invention was applied to detecting reactive metabolites of known test compounds, more particularly to test compounds which are known to produce "soft" and/or "hard" metabolites, scanning the neutral loss mass spectrum at a loss of 129 Da, and using the isotopically labeled compound of formula (I-IS), which differs from the corresponding non-isotopically labeled compound of formula (I) by 8 Da units.

EXAMPLE 2

Diclofenac

Diclofenac was selected as a test compound to demonstrate the applicability of the method of the present invention to the detection of soft reactive metabolite(s).

The formation of two reactive metabolites of diclofenac and the corresponding adducts, is as outlined in Scheme E1, below. In the reaction outlined below, the reactive metabolites of diclofenac form adducts with the non-isotopically compound of formula (I) and the isotopically labeled compound of formula (I-IS) through the —SH moiety. For clarity, only adducts with the non-isotopically labeled compound of formula (I) are shown below. One skilled in the art will recognize that the adducts with the isotopically-labeled compound of formula (I-IS) would have the same structure, differing only in the isotopic labeling.

Scheme E1

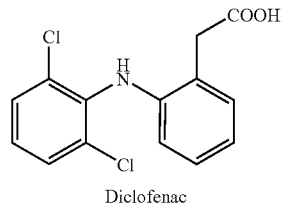

Diclofenac

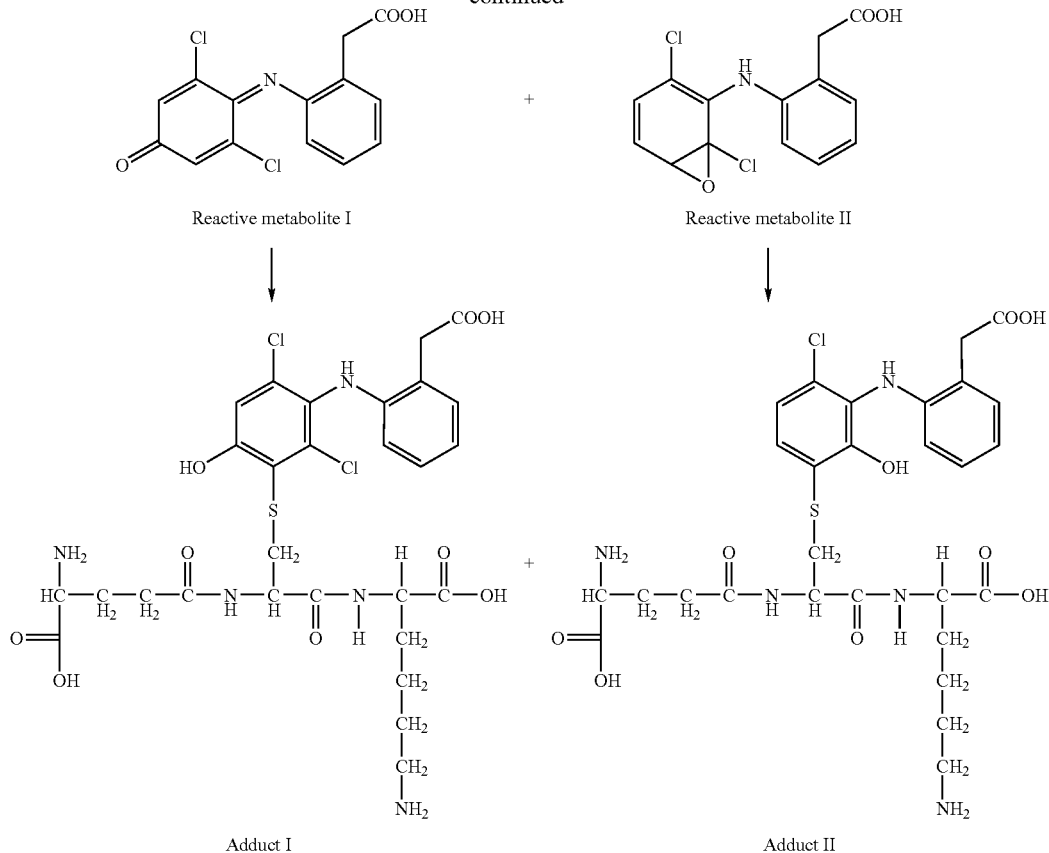

Adduct I          Adduct II

Figure 1B:
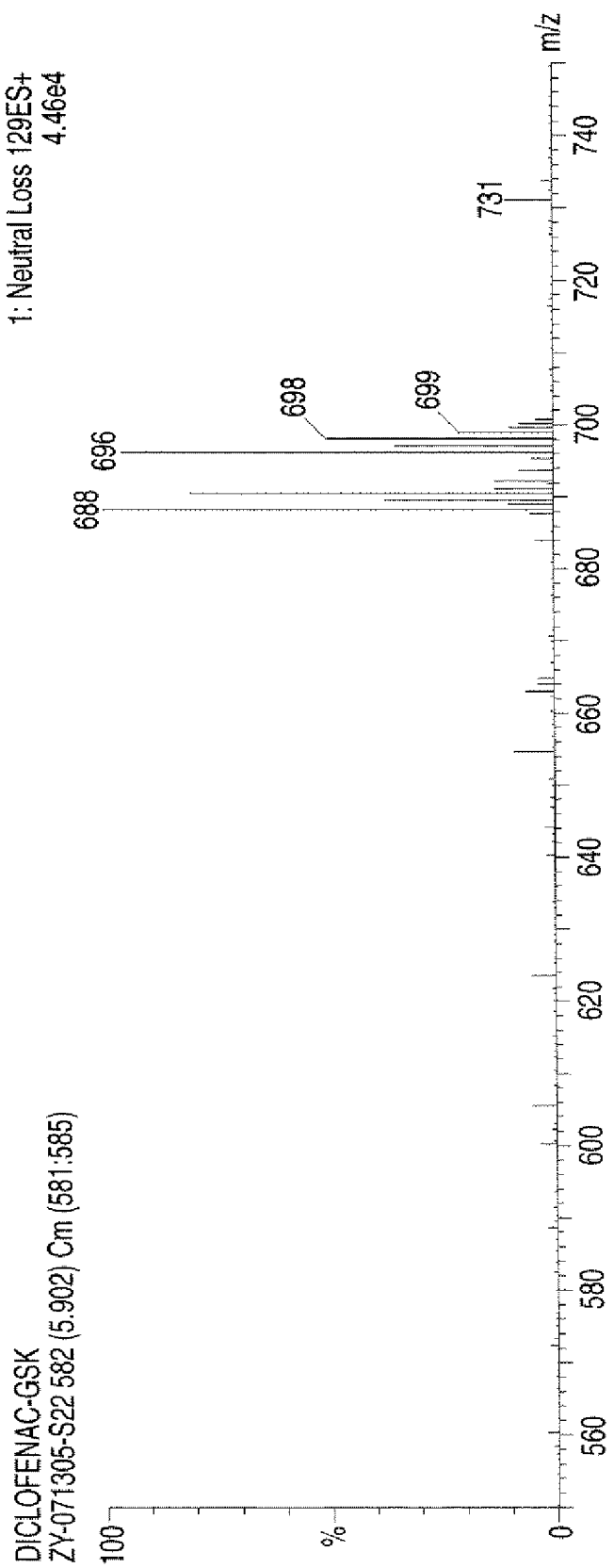
FIG. 1B illustrates the neutral loss tandem mass spectrum of adduct I derived from diclofenac.

FIG. 1A shows the total ion chromatogram (MS) of the neutral loss scanning of 129 Da obtained for the reaction mixture. Several components showed a positive response to the neutral scan, and two of the components showed the expected isotope doublet (with a mass difference of 8 Da). Adduct I was eluted at a retention time of 5.9 min and displayed the characteristic isotopic doublet at m/z 688 and 696, as shown in FIG. 1B, whereas Adduct II appeared at a retention time of 5.8 min and exhibited the characteristic isotopic doublet ay m/z 654 and 662 Da, as shown in FIG. 1C.

EXAMPLE 3

Clozapine

Clozapine was selected as a test compound to demonstrate the applicability of the method of the present invention to the detection of soft reactive metabolite(s).

The formation of a single reactive metabolite of clozapine and the corresponding adduct, is as outlined in Scheme E2, below. In the reaction outlined below, the reactive metabolite of clozapine forms an adduct with the non-isotopically compound of formula (I) and the isotopically labeled compound of formula (I-IS) through the —SH moiety. For clarity, only adducts with the non-isotopically labeled compound of formula (I) are shown below. One skilled in the art will recognize that the adducts with the isotopically-labeled compound of formula (I-IS) would have the same structure, differing only in the isotopic labeling.

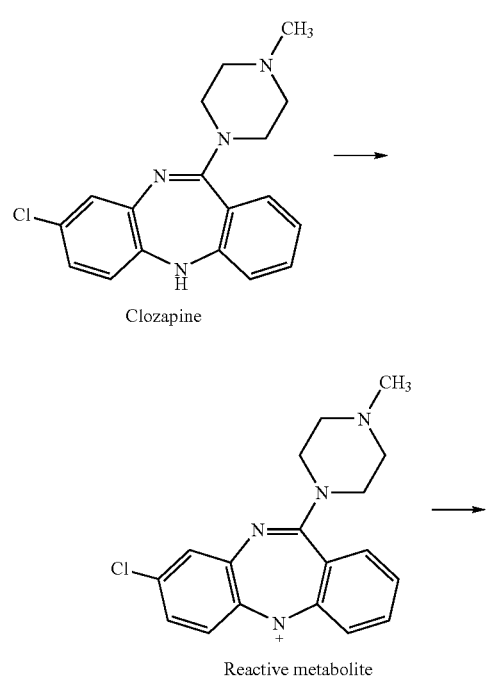

Scheme E2

Clozapine

Reactive metabolite

-continued

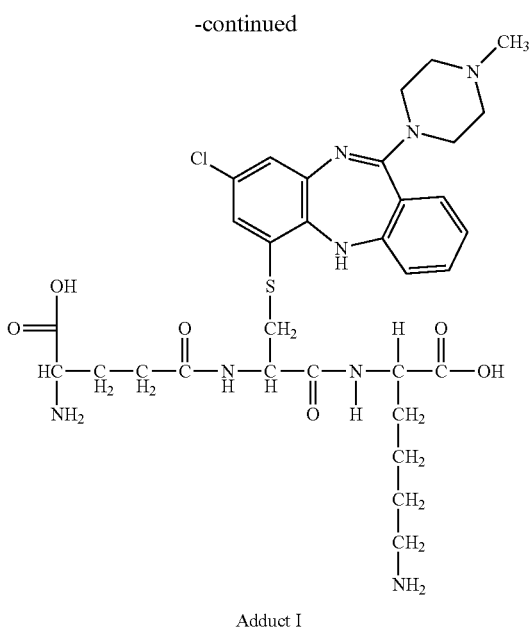

Adduct I

Figure 2A:
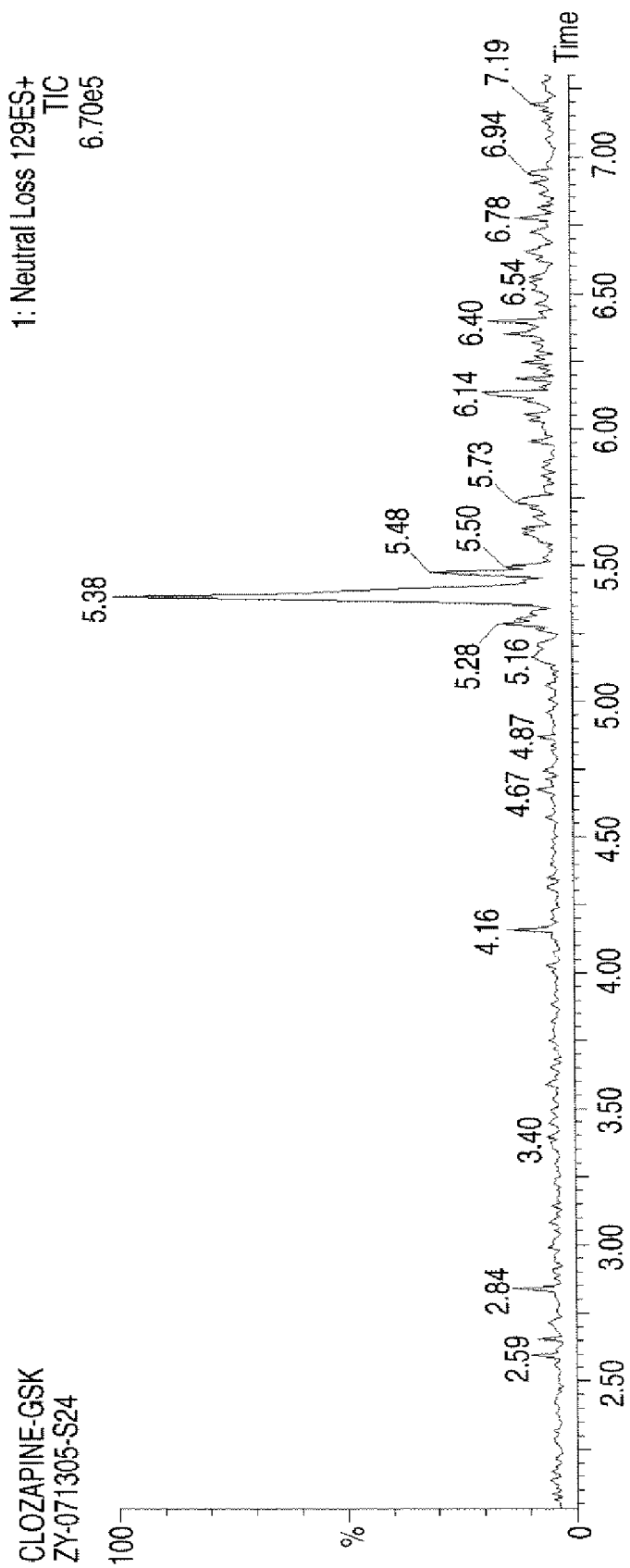
FIG. 2A illustrates the total ion chromatogram of neutral loss scanning of 129 Da for clozapine.
Figure 2B:
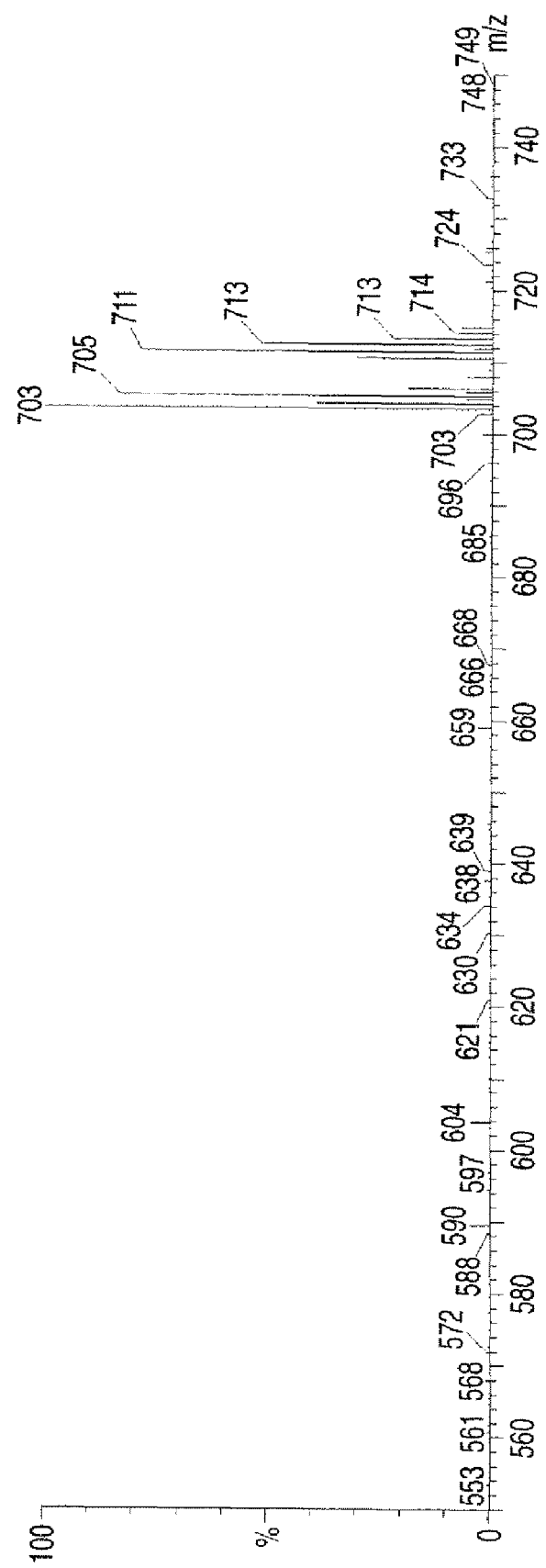
FIG. 2B illustrates the neutral loss tandem mass spectrum of adduct I derived from clozapine.

FIG. 2A shows the total ion chromatogram (MS) of the neutral loss scanning of 129 Da obtained for the reaction mixture. Several components showed a positive response to the neutral scan, but only one component, at a retention time of 5.4 min, displayed the characteristic isotopic doublet at m/z 703 and 711 Da, as shown in FIG. 2B.

EXAMPLE 4 p-Cresol p-Cresol was selected as a test compound to demonstrate the applicability of the method of the present invention to the detection of soft reactive metabolite(s).

The formation of two reactive metabolites of p-cresol and the corresponding adducts, is as outlined in Scheme E3, below. In the reaction outlined below, the reactive metabolites of p-cresol form adducts with the non-isotopically compound of formula (I) and the isotopically labeled compound of formula (I-IS) through the —SH moiety. For clarity, only adducts with the non-isotopically labeled compound of formula (I) are shown below. One skilled in the art will recognize that the adducts with the isotopically-labeled compound of formula (I-IS) would have the same structure, differing only in the isotopic labeling.

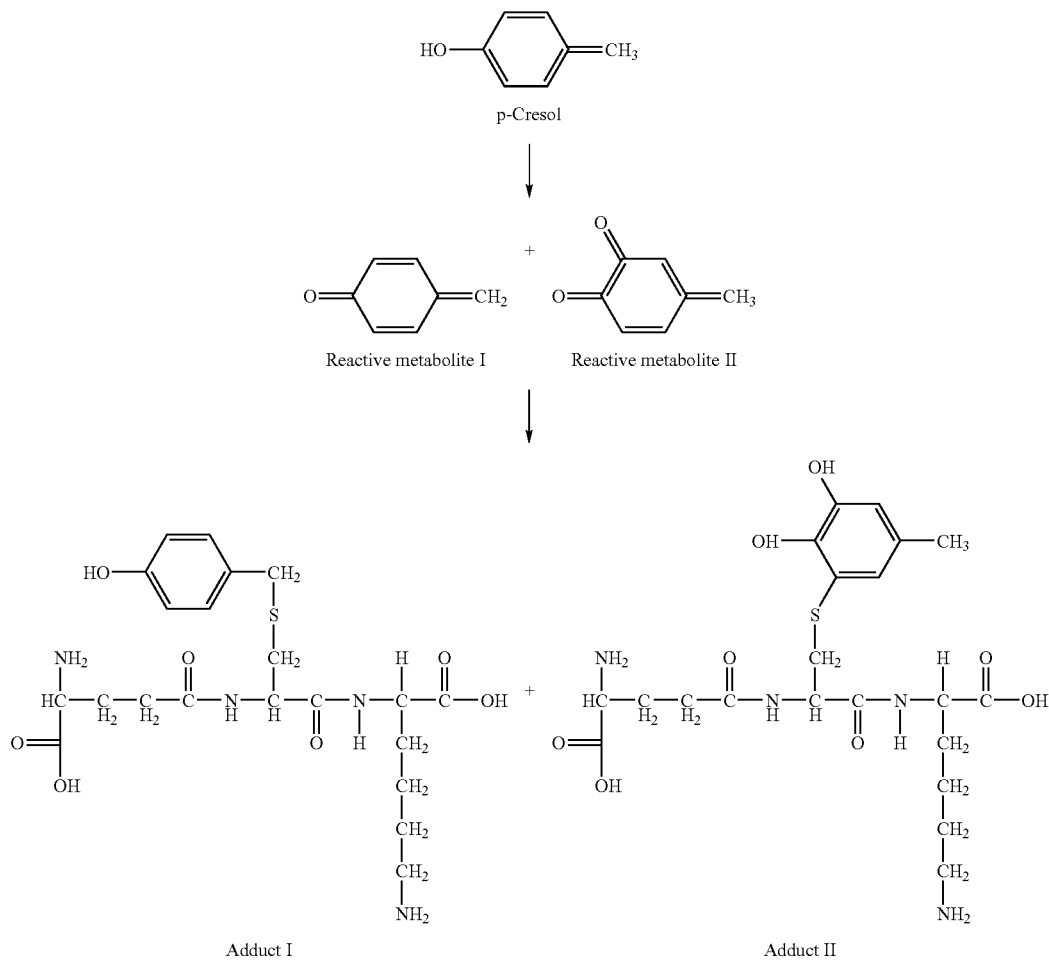

Figure 3A:
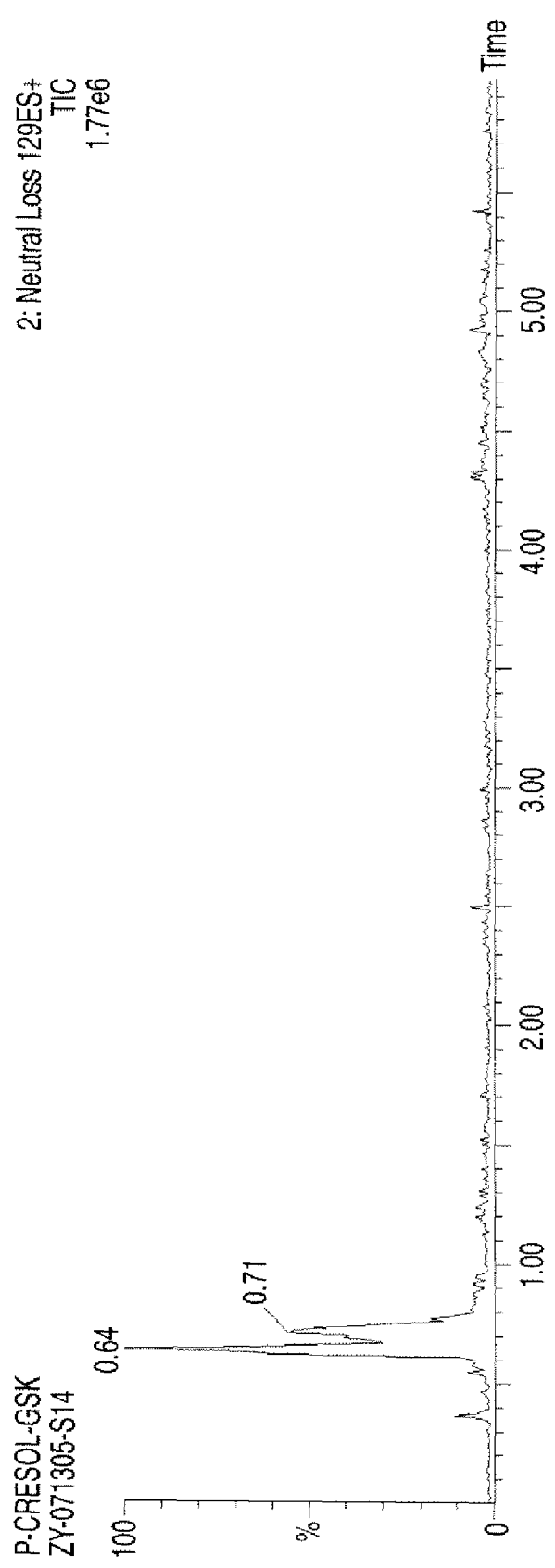
FIG. 3A illustrates the total ion chromatogram of neutral loss scanning of 129 Da for p-cresol.
Figure 3B:
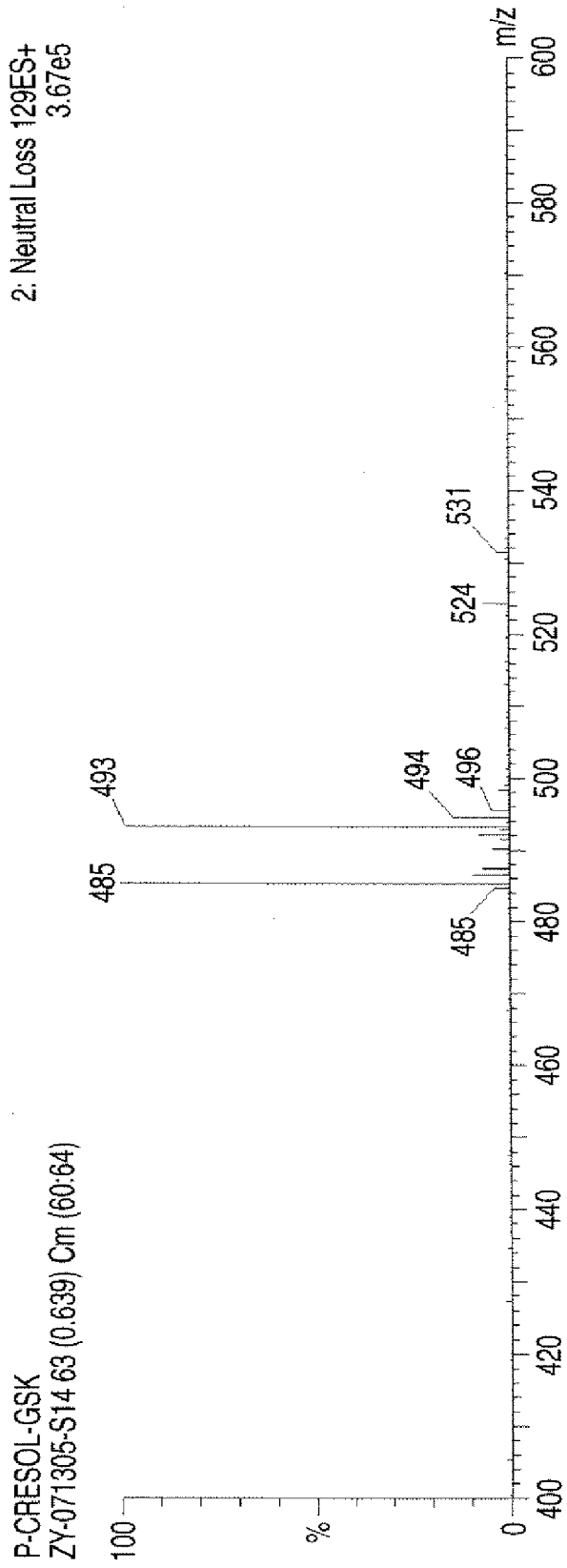
FIG. 3B illustrates the neutral loss tandem mass spectrum of adduct I derived from p-cresol.
Figure 3C:
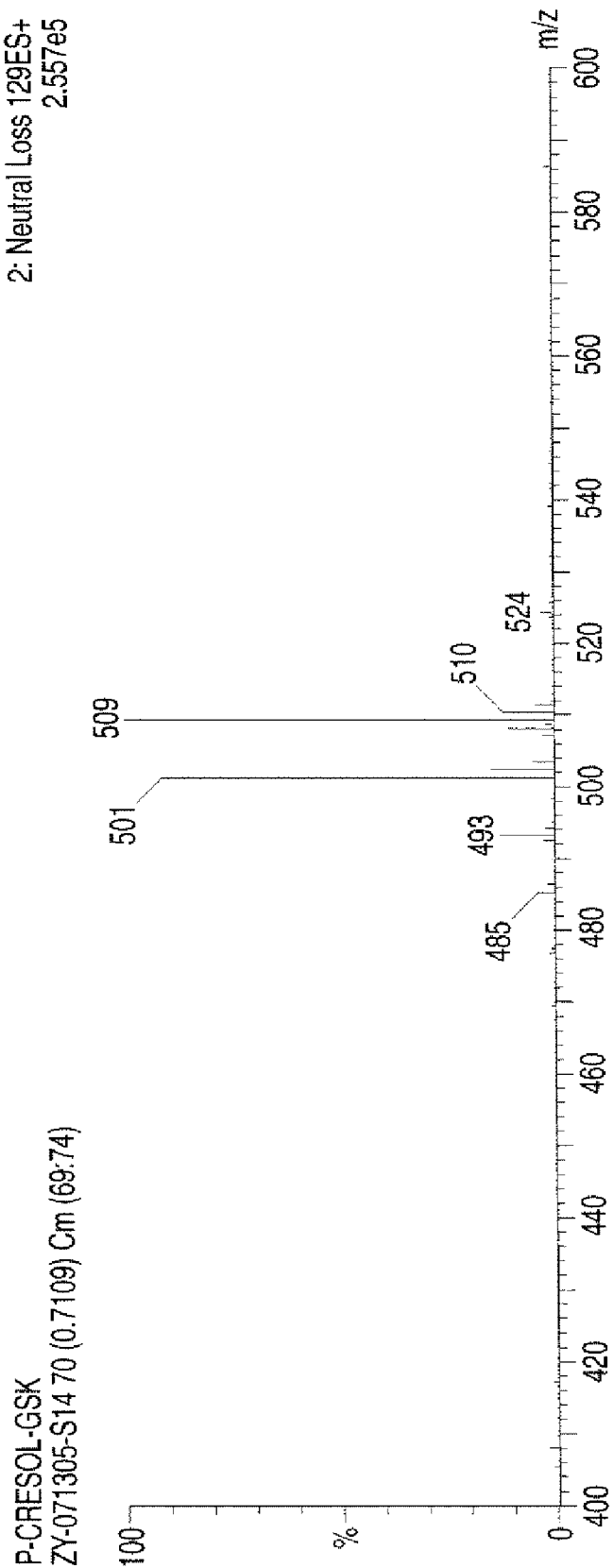
FIG. 3C illustrates the neutral loss tandem mass spectrum of adduct II derived from p-cresol.

FIG. 3A shows the total ion chromatogram (MS) of the neutral loss scanning of 129 Da obtained for the reaction mixture. Two components showed the characteristic isotopic doublet. Adduct I, with a retention time of 0.64 min, showed the isotopic doublet at m/z 485 and 493 Da, as shown in FIG. 3B. Adduct II, with a retention time of 0.71 min, showed the isotopic doublet at m/z 501 and 509 Da, as shown in FIG. 3C.

EXAMPLE 5

Omeprazole

Omeprazole was selected as a test compound to demonstrate the applicability of the method of the present invention to the detection of soft reactive metabolite(s).

The formation of a single reactive metabolites of omerprazole and the corresponding adduct, is as outlined in Scheme E4, below. In the reaction outlined below, the reactive metabolite of omerprazole forms and adduct with the non-isotopically compound of formula (I) and the isotopically labeled compound of formula (I-IS) through the —SH moiety. For clarity, only adducts with the non-isotopically labeled compound of formula (I) are shown below. One skilled in the art will recognize that the adducts with the isotopically-labeled compound of formula (I-IS) would have the same structure, differing only in the isotopic labeling.

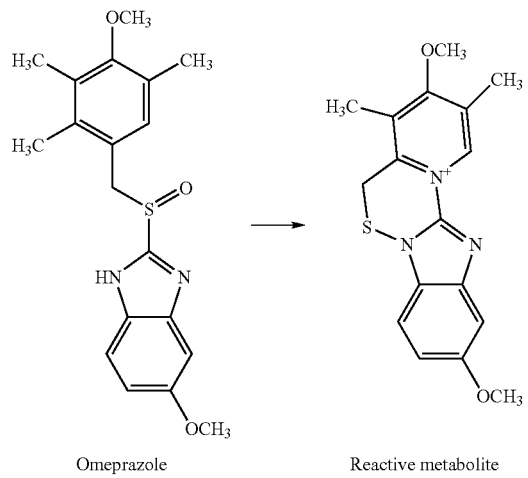

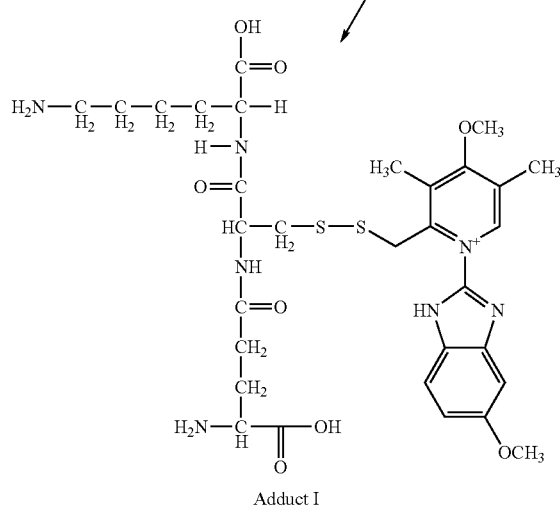

Figure 4A:
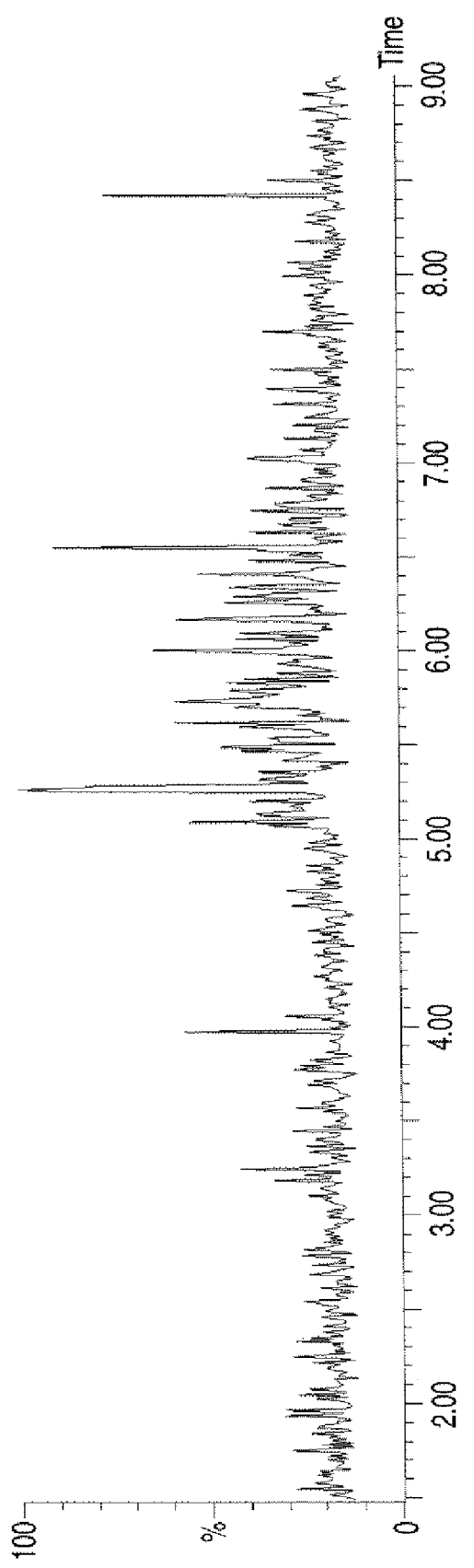
FIG. 4A illustrates the total ion chromatogram of neutral loss scanning of 129 Da for omeprazole.
Figure 4B:
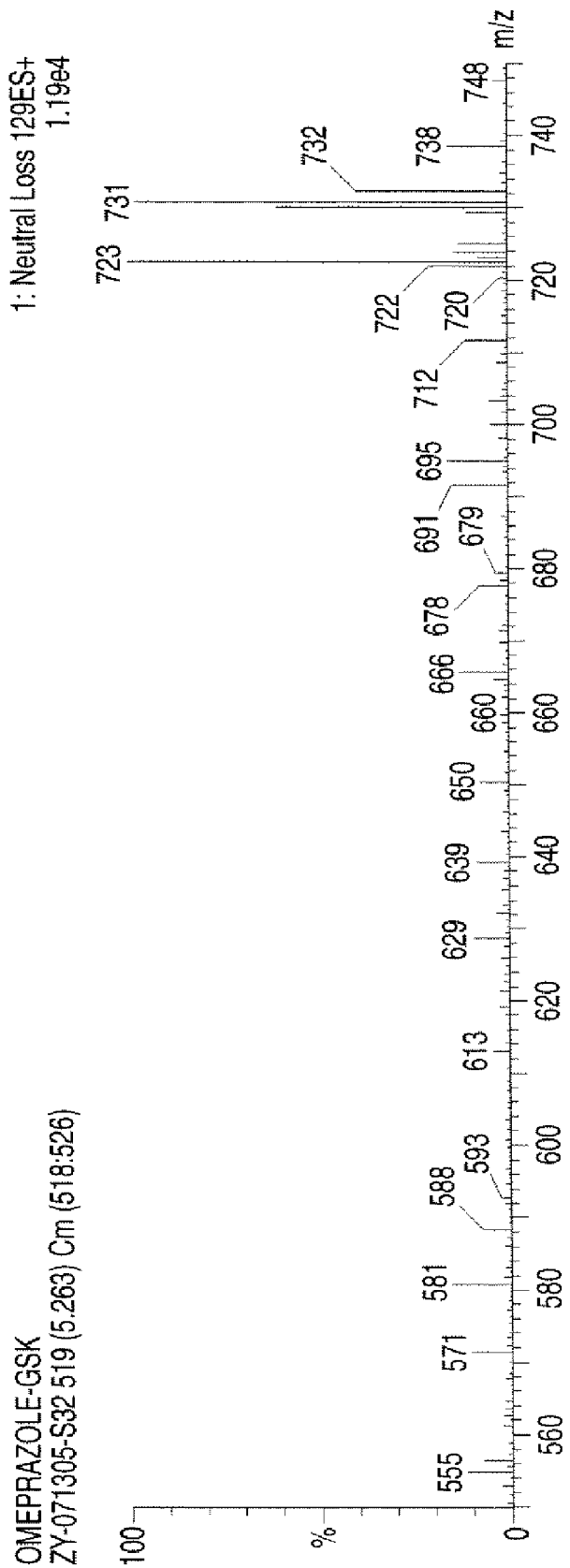
FIG. 4B illustrates the neutral loss tandem mass spectrum of adduct I derived from omeprazole.

FIG. 4A shows the total ion chromatogram (MS) of the neutral loss scanning of 129 Da obtained for the reaction mixture. Only one component at a retention time of 5.3 min displayed the characteristic isotopic doublet at m/z 723 and 731 Da, as shown in FIG. 4B.

EXAMPLE 6

Furan

Furan was selected as a test compound to demonstrate the applicability of the method of the present invention to the detection of hard reactive metabolite(s).

The formation of a single reactive metabolite of furan and the corresponding adduct, is as outlined in Scheme E5, below. In the reaction outlined below, the reactive metabolite of furan forms an adduct with the non-isotopically compound of formula (I) and the isotopically labeled compound of formula (I-IS) through both the —SH moiety and the terminal —NH$_2$ moiety. For clarity, only adducts with the non-isotopically labeled compound of formula (I) are shown below. One skilled in the art will recognize that the adducts with the isotopically-labeled compound of formula (I-IS) would have the same structure, differing only in the isotopic labeling.

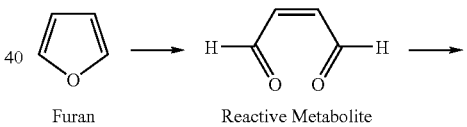

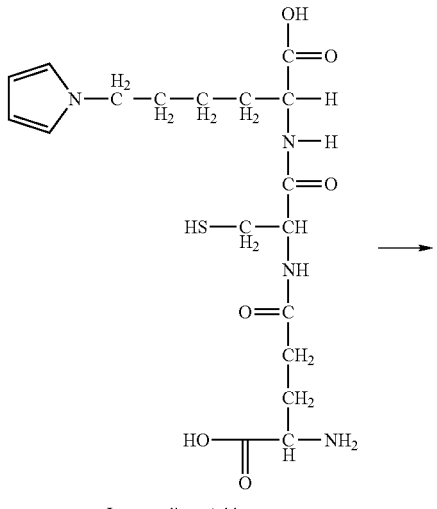

Intermediate Adduct

-continued

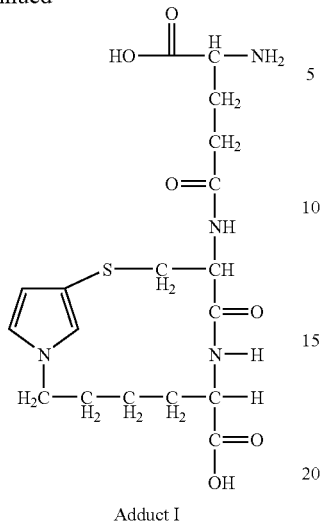

Adduct I

Figure 5A:
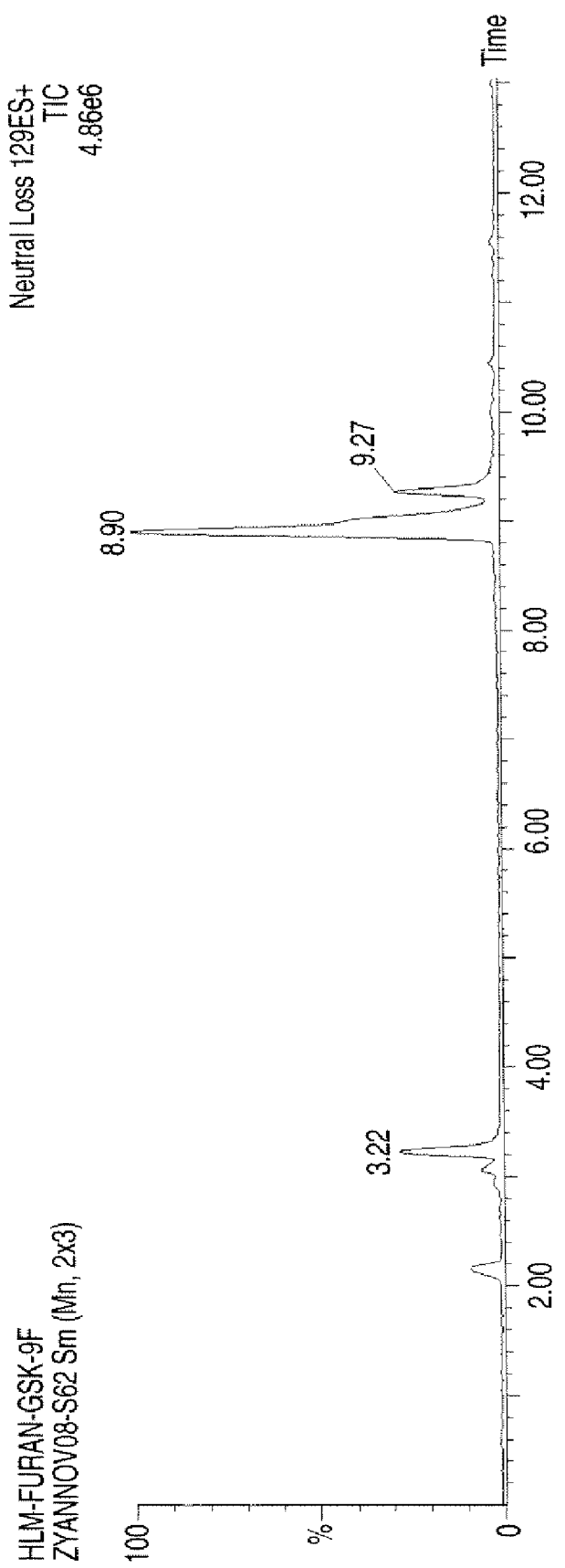
FIG. 5A illustrates the total ion chromatogram of neutral loss scanning of 129 Da for furan.
Figure 5B:
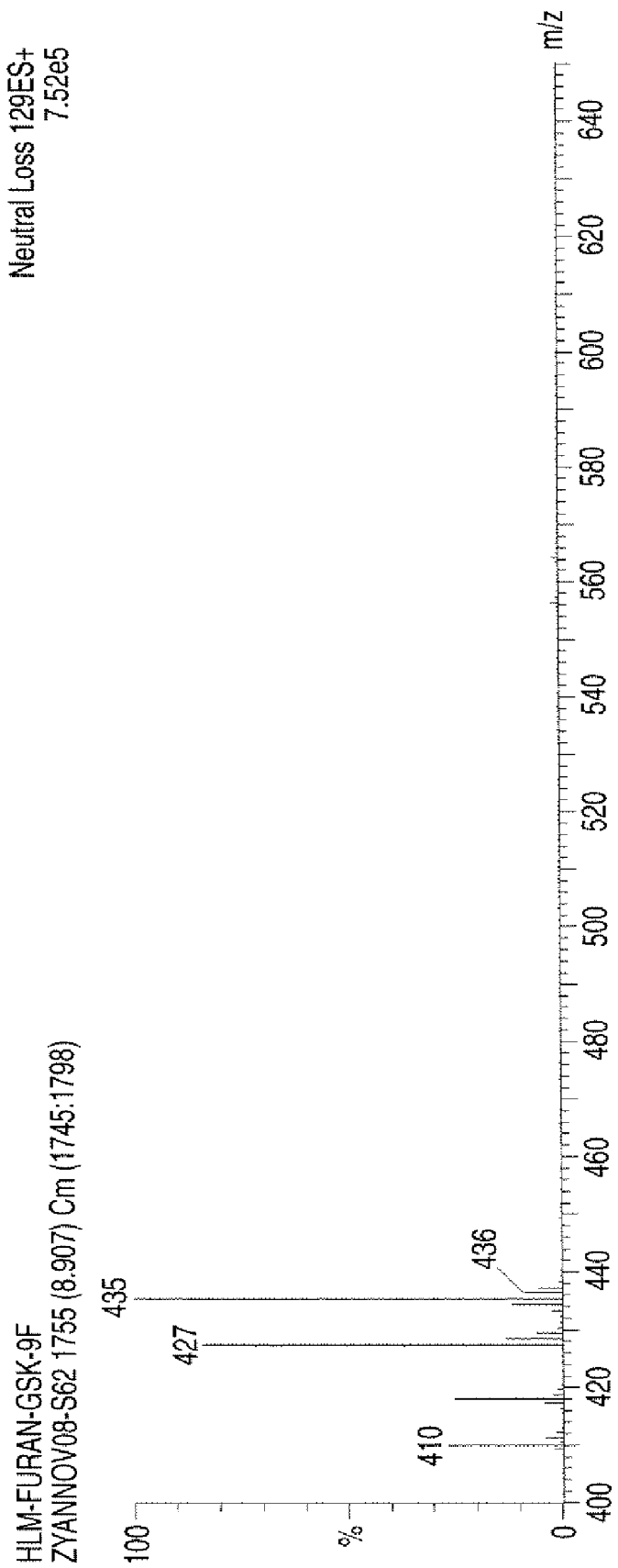
FIG. 5B illustrates the neutral loss tandem mass spectrum of adduct I derived from furan.

FIG. 5A shows the total ion chromatogram (MS) of the neutral loss scanning of 129 Da obtained for the reaction mixture. The component eluted at a retention time of 8.9 min displayed the characteristic isotopic doublet at m/z 427 and 435 Da, as shown in FIG. 5B.

EXAMPLE 7

2-Methylfuran

2-Methylfuran was selected as a test compound to demonstrate the applicability of the method of the present invention to the detection of hard reactive metabolite(s).

The formation of a single reactive metabolite of 2-methylfuran and the corresponding two structural isomer adducts, is as outlined in Scheme E6, below. In the reaction outlined below, the reactive metabolite of 2-methylfuran forms two structural isomer adducts with the non-isotopically compound of formula (I) and the isotopically labeled compound of formula (I-IS) through both the —SH Moiety and the terminal —NH$_2$ moiety. For clarity, only adducts with the non-isotopically labeled compound of formula (I) are shown below. One skilled in the art will recognize that the adducts with the isotopically-labeled compound of formula (I-IS) would have the same structure, differing only in the isotopic labeling. One skilled in the art will further recognize that the two structural isomer adducts formed in this experiment will produce approximately identical mass spectra.

Scheme E6

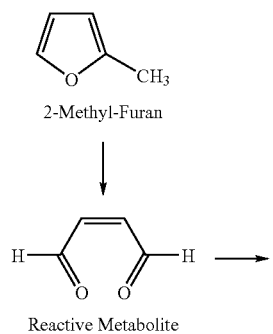

-continued

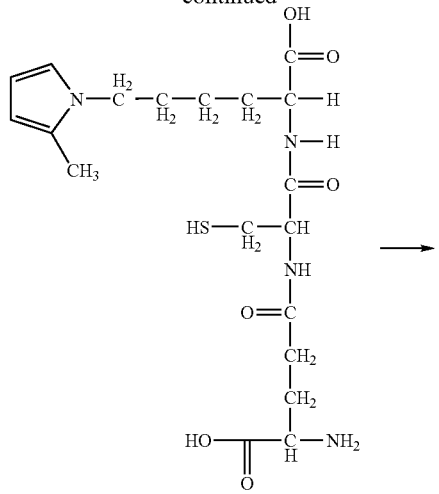

Intermediate Adduct

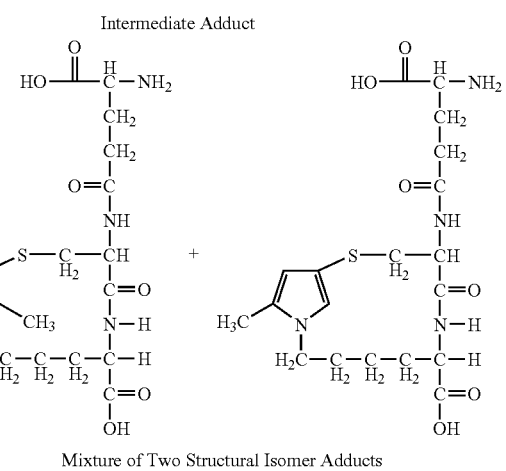

Mixture of Two Structural Isomer Adducts

Figure 6A:
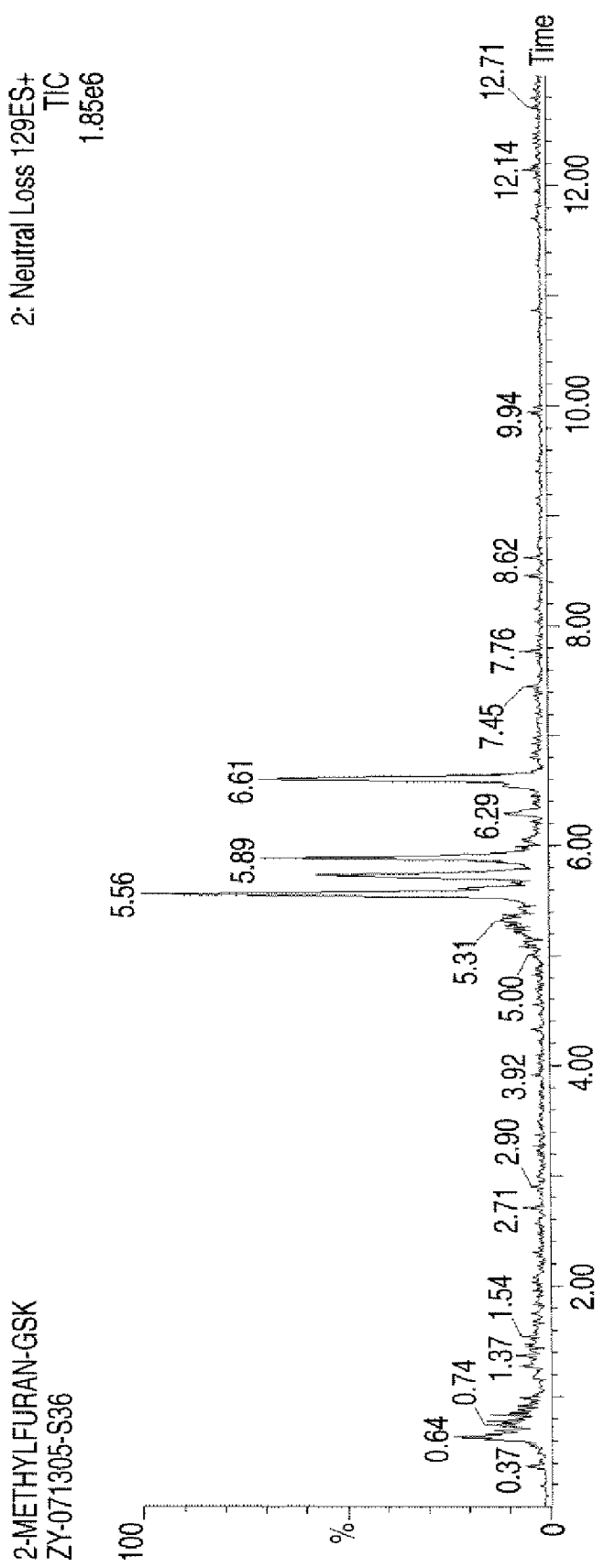
FIG. 6A illustrates the total ion chromatogram of neutral loss scanning of 129 Da for 2-methylfuran.
Figure 6B:
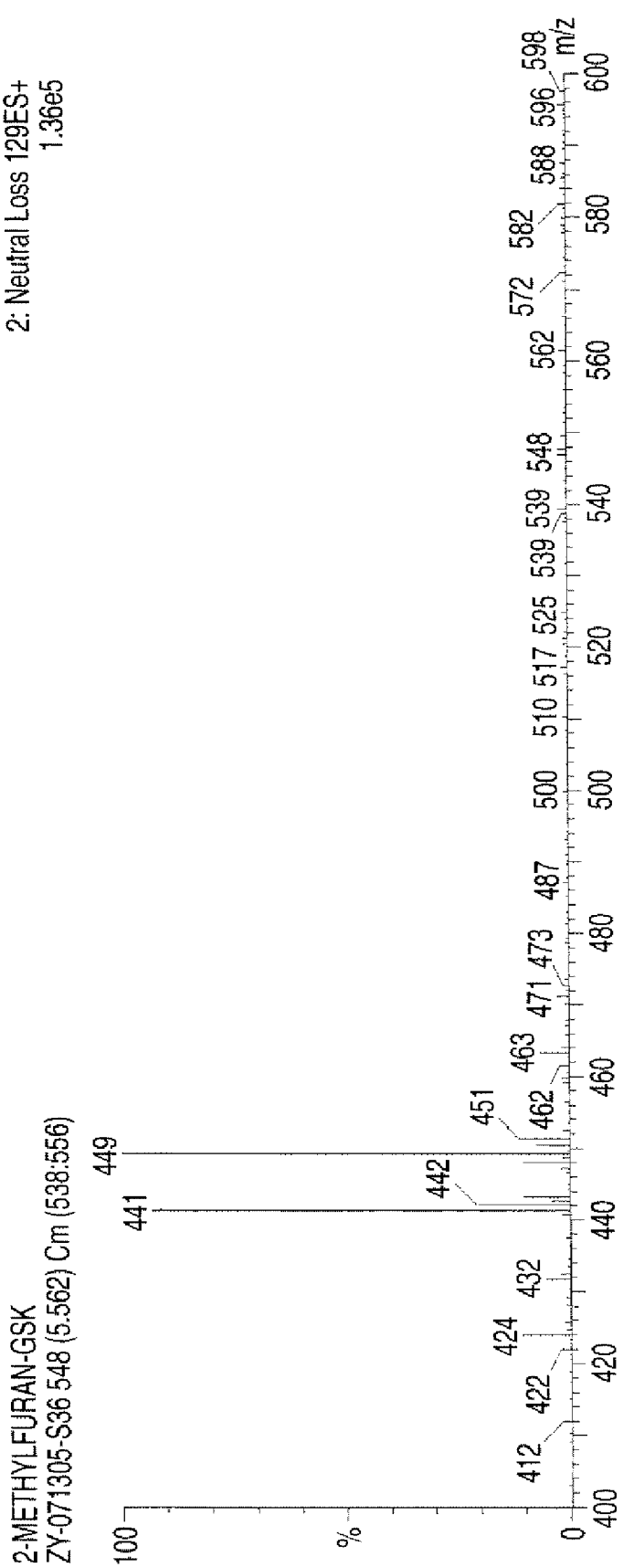
FIG. 6B: NL tandem mass spectrum of isomeric adducts derived from 2-methylfuran.

FIG. 6A shows the total ion chromatogram (MS) of the neutral loss scanning of 129 Da obtained for the reaction mixture. Two isomeric adducts (structural isomers) with retention times of 5.6 min and 5.9 min each displayed a characteristic isotopic doublet at m/z 441 and 449 Da, as shown in FIG. 6B.

EXAMPLE 8

2-Menthofuran

Menthofuran was selected as a test compound to demonstrate the applicability of the method of the present invention to the detection of hard reactive metabolite(s).

The formation of a single reactive metabolite of menthofuran and the corresponding adduct, is as outlined in Scheme E7, below. In the reaction outlined below, the reactive metabolite of menthofuran forms an adduct with the non-isotopically compound of formula (I) and the isotopically labeled compound of formula (I-IS) through the terminal —NH$_2$ moiety. For clarity, only adducts with the non-isotopically labeled compound of formula (I) are shown below. One skilled in the art will recognize that the adducts with the isotopically-labeled compound of formula (I-IS) would have the same structure, differing only in the isotopic labeling.

29

Scheme E7

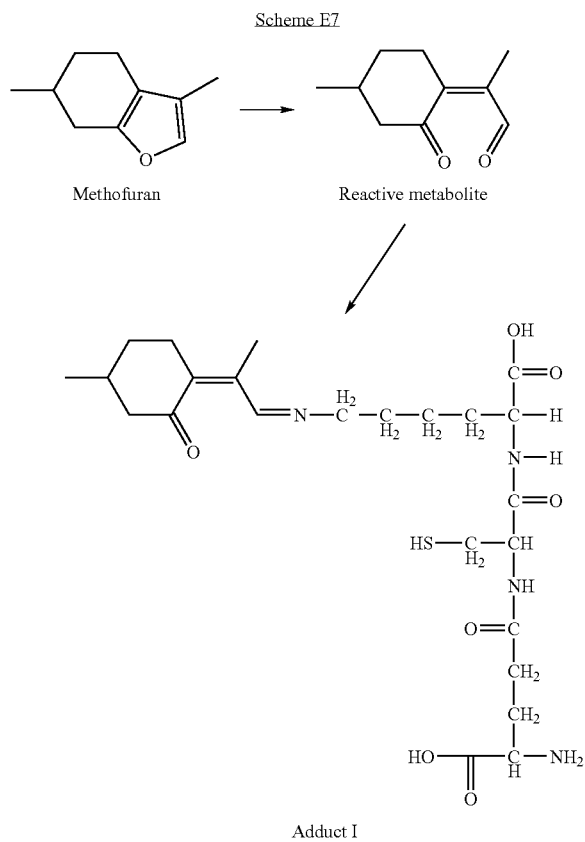

Methofuran → Reactive metabolite → Adduct I

Figure 7A:
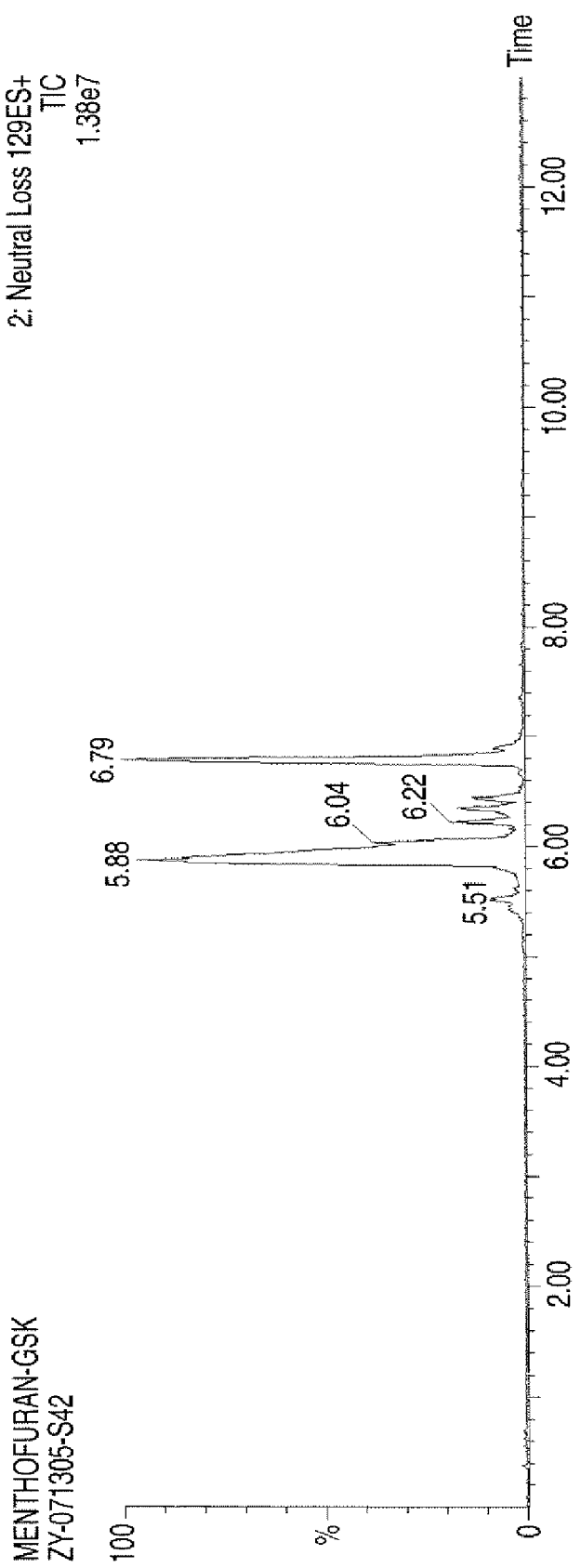
FIG. 7A illustrates the total ion chromatogram of neutral loss scanning of 129 Da for menthofuran.
Figure 7B:
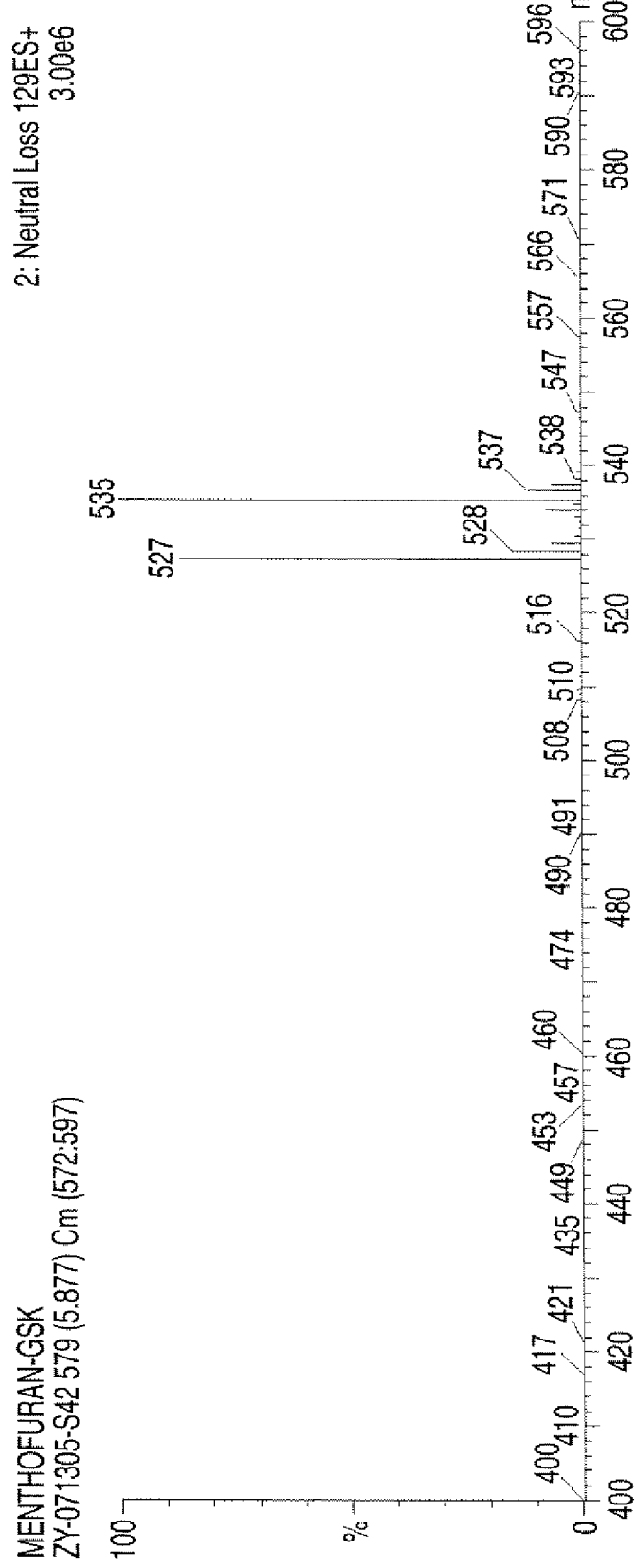
FIG. 7B illustrates the neutral loss tandem mass spectrum of adduct I derived from menthofuran.

FIG. 7A shows the total ion chromatogram (MS) of the neutral loss scanning of 129 Da obtained for the reaction mixture. One component at a retention time of 5.9 min displayed the characteristic isotopic doublet at m/z 527 and 535 Da, as shown in FIG. 5B.

30

EXAMPLE 9

2-(2-Thienyl)-furan 2-(2-Thienyl)-furan was selected as a test compound to demonstrate the applicability of the method of the present invention to the detection of both hard and soft reactive metabolite(s).

The formation of reactive metabolites of 2-(2-thienyl)-furan and subsequent adducts with a mixture of the compound of formula (I) and isotopically labeled compound of formula (I-IS), hereinafter referred to as "trapping agent GSK" is as outlined in Scheme E8 and E9, below. More specifically, Scheme 8 shows the opening of the furan ring which generates a hard reactive metabolite (H1), the epoxidation of the thiophene ring which generates a soft reactive metabolite (S1), and the formation of the corresponding adducts. Additionally, Scheme 9 shows the isomerization of reactive metabolite (S1) to form a second hard reactive metabolite (H2), and formation of its corresponding adduct. The (H1) reactive metabolite forms an adduct with the non-isotopically compound of formula (I) and the isotopically labeled compound of formula (I-IS) through both the —SH moiety and the terminal —NH$_2$ moiety; the (S1) reactive metabolite forms an adduct with the non-isotopically compound of formula (I) and the isotopically labeled compound of formula (I-IS) through both the —SH moiety; and the (H3) reactive metabolite forms an adduct with the non-isotopically compound of formula (I) and the isotopically labeled compound of formula (I-IS) through the terminal —NH$_2$ moiety. For clarity, only adducts with the non-isotopically labeled compound of formula (I) are shown below. One skilled in the art will recognize that the adducts with the isotopically-labeled compound of formula (I-IS) would have the same structure, differing only in the isotopic labeling.

Scheme E8

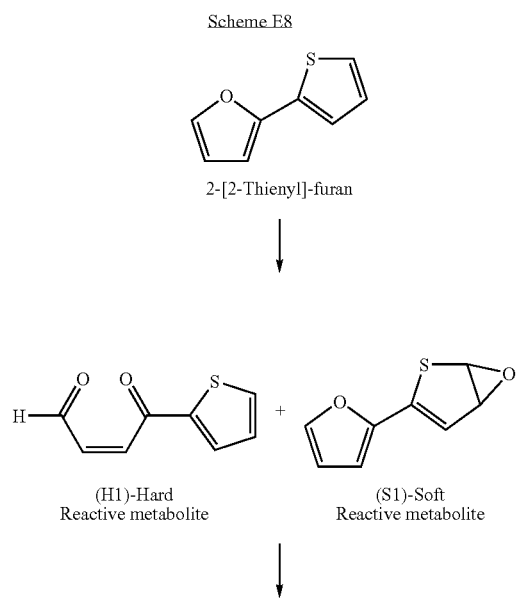

2-[2-Thienyl]-furan

↓

(H1)-Hard Reactive metabolite    +    (S1)-Soft Reactive metabolite

↓

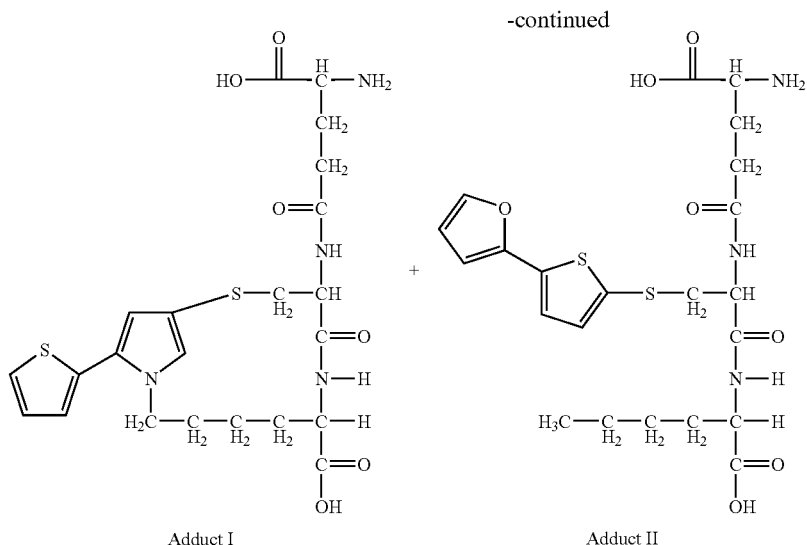

Adduct I + Adduct II

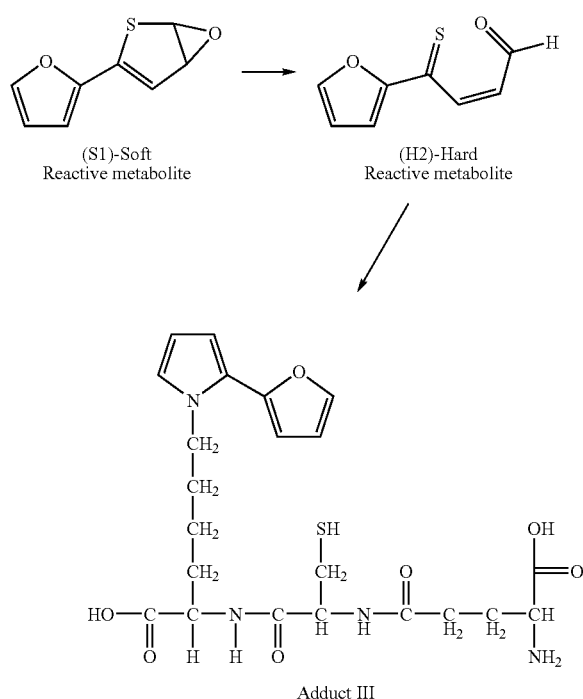

Adduct III

Figure 8A:
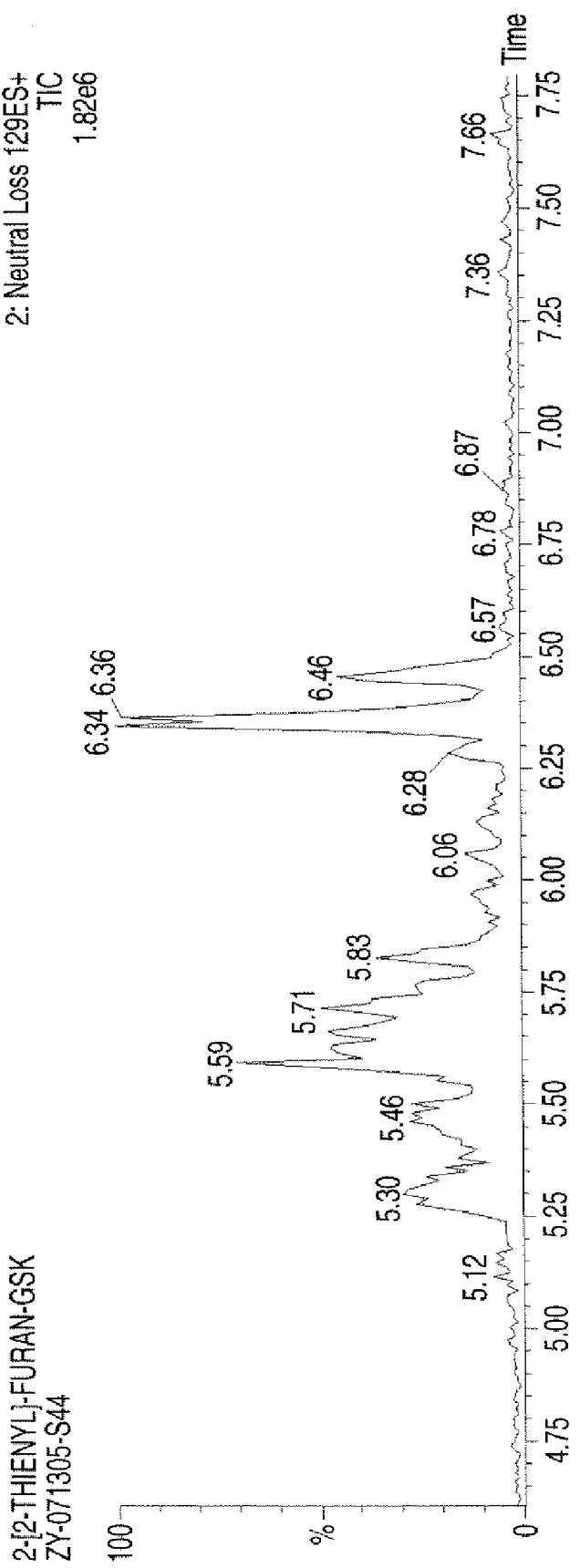
FIG. 8A illustrates the total ion chromatogram of neutral loss scanning of 129 Da for 2-[2-thienyl]-furan.
Figure 8C:
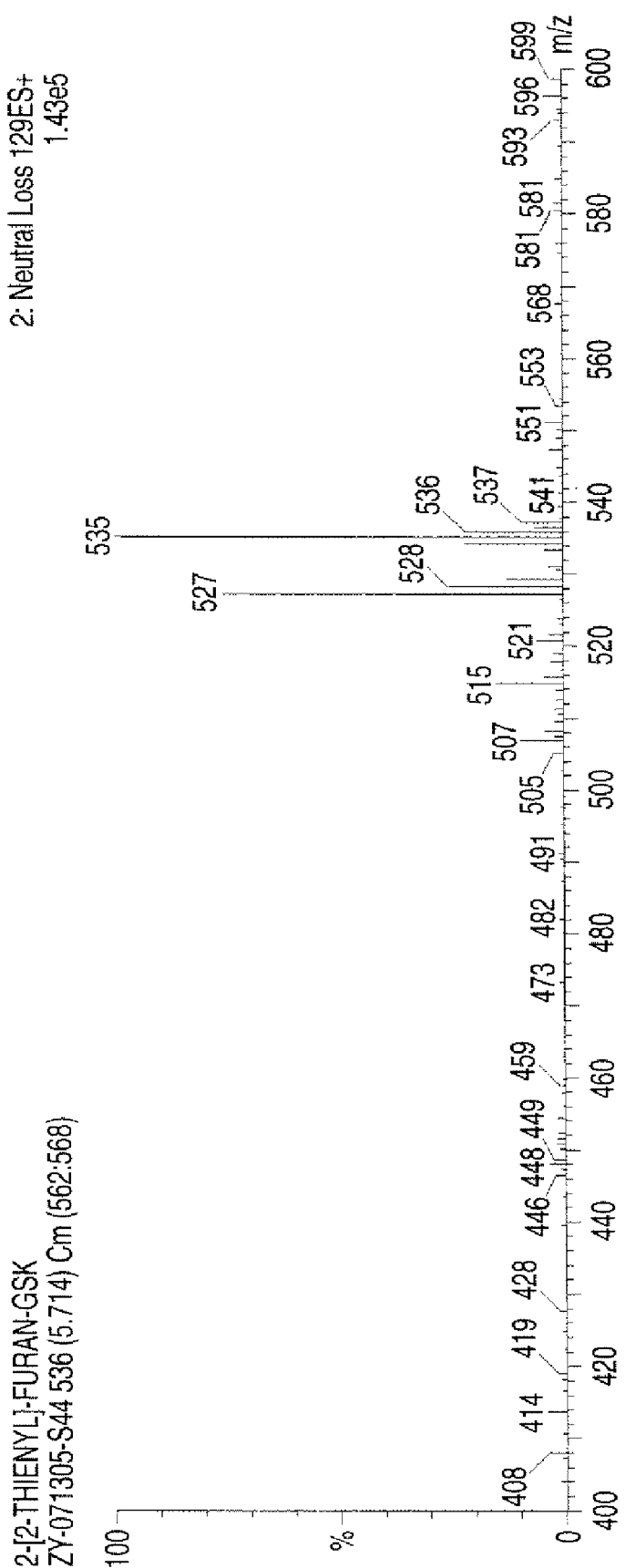
FIG. 8C illustrates the neutral loss tandem mass spectrum of adduct II derived from 2-[2-thienyl]-furan.

FIG. 8A shows the total ion chromatogram (MS) of the neutral loss scanning of 129 Da obtained for the reaction mixture. Adduct I, with a retention time of 6.5 min, showed the characteristic isotopic doublet at m/z 509 and 517 Da, as shown in FIG. 8B; Adduct II showed the characteristic isotopic doublet at m/z 527 and 535 Da, as shown in FIG. 8C; and Adduct III showed the characteristic isotopic doublet at m/z 495 and 503 Da, as shown in FIG. 8D.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. An isotopically labeled compound of formula (I)

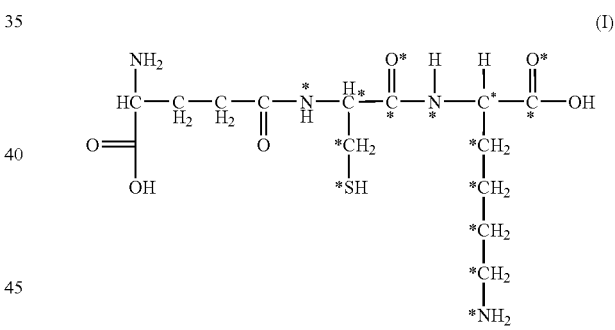

wherein one or more of the carbon, nitrogen, oxygen, sulfur or non-exchangeable hydrogen atoms on the starred groups are isotopically enriched.

2. A compound as in claim 1, wherein the isotopically labeled compound of formula (I) is labeled with at least one isotope selected from the group consisting of $^{13}C$, $^{15}N$, $^{18}O$ and $^{2}H$.

3. A compound as in claim 2, wherein the isotopically labeled compound of formula (I) is labeled with one to ten isotopes selected from the group consisting of $^{13}C$ and $^{15}N$.

4. A compound as in claim 3, wherein six carbon atoms are isotopically labeled with $^{13}C$ isotopes and two nitrogen atoms are isotopically labeled with $^{15}N$ isotopes.

5. An isotopically enriched compound of formula (I-IS)

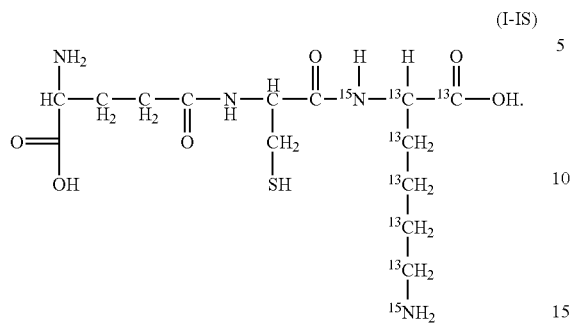

6. A method for detecting reactive metabolites of a test compound comprising
   (a) incubating a test compound with an isotopically labeled compound of formula (I)

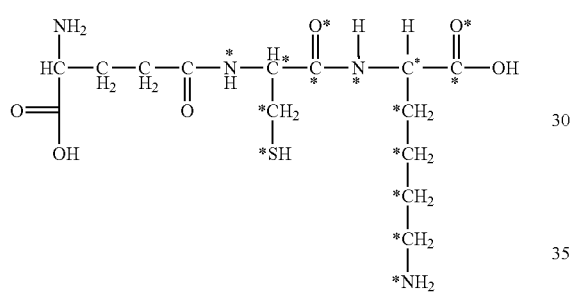

wherein one or more of the carbon, nitrogen, oxygen, sulfur or non-exchangeable hydrogen atoms on the starred groups are isotopically enriched;
and a drug metabolizing enzyme; to yield a product mixture comprising one or more adducts; and
   (b) detecting the one or more adducts of Step (a).

7. A method for detecting reactive metabolites of a test compound comprising
   (a) incubating a test compound with a mixture comprising a compound of formula (I)

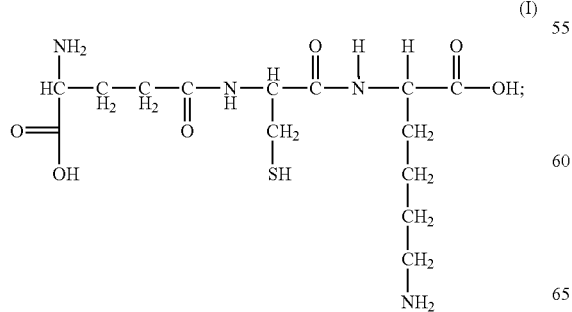

an isotopically labeled compound of formula (I)

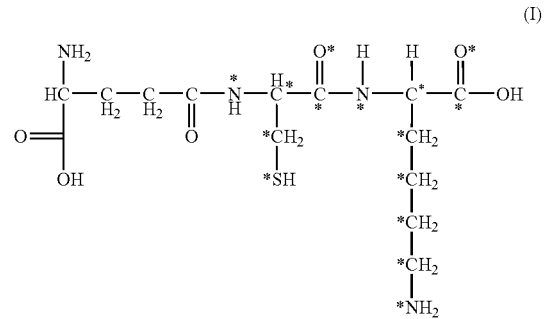

wherein one or more of the carbon, nitrogen, oxygen, sulfur or non-exchangeable hydrogen atoms on the starred groups are isotopically enriched; and a drug metabolizing enzyme;
to yield a product mixture comprising one or more adducts; and
   (b) detecting the one or more adducts of Step (a).

8. A method for detecting reactive metabolites of a test compound comprising
   (a) incubating a test compound with a mixture comprising a compound of formula (I)

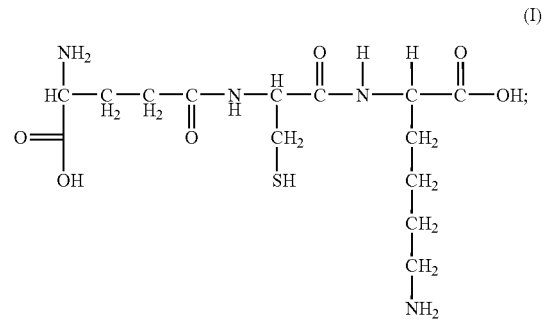

an isotopically labeled compound of formula (I)

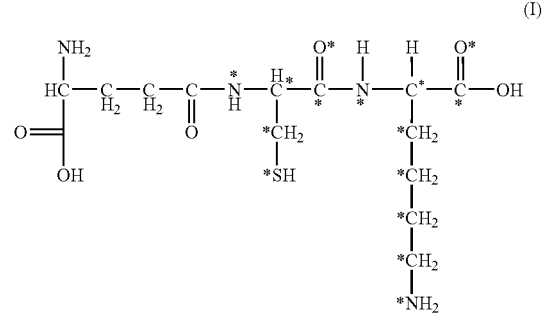

wherein one or more of the carbon, nitrogen, oxygen, sulfur or non-exchangeable hydrogen atoms on the starred groups are isotopically enriched;
and a drug metabolizing enzyme;
to yield a product mixture comprising one or more adducts;
   (b) detecting one or more isotopic doublets in a neutral loss mass spectrum of the one or more adducts produced in Step (a), wherein the doublet differs in mass by the difference in mass between the compound of formula (I) and the isotopically labeled compound of formula (I).

9. The method of claim 8, wherein the isotopically labeled compound of formula (I) is labeled with at least one isotope selected from the group consisting of $^{13}C$, $^{15}N$, $^{18}O$ and $^{2}H$.

10. The method of claim 9, wherein the isotopically labeled compound of formula (I) is labeled with one to ten isotopes selected from the group consisting of $^{13}C$ and $^{15}N$.

11. The method of claim 8, wherein the isotopically labeled compound of formula (I) is labeled with six $^{13}C$ atoms and two $^{15}N$ atoms.

12. The method of claim 8, wherein the molar ratio of the compound of formula (I) to the isotopically labeled compound of formula (I) is about 1:1.

13. The method of claim 12, wherein the isotopic doublet differs by a mass of 8 mass units.

14. The method of claim 8, wherein the drug metabolizing enzyme is human liver microsomes.

15. The method of claim 8, wherein the drug metabolizing enzyme is cytochrome P450 enzymes in combination with NADPH co-factor or cytochrome P450 enzymes in combination with NADPH regenerating system.

16. The method of claim 8, wherein the neutral loss mass spectrum is measured using ESI-MS/MS or LS/MS.

17. The method of claim 8, wherein the isotopically enriched compound of formula (I) is the compound of formula (I-IS)

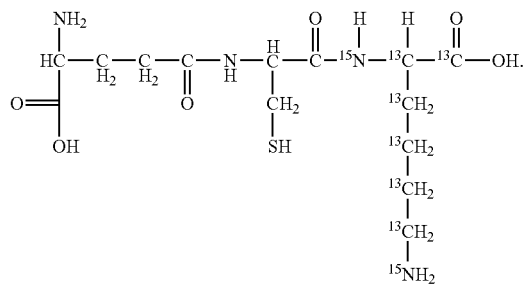

(I-IS)

18. The method of claim 17, wherein the molar ratio of the compound of formula (I) to the isotopically enriched compound of formula (I-IS) is about 1:1.

19. The method of claim 18, wherein the drug metabolizing enzyme is selected from the group consisting of human liver microsomes, cytochrome P450 enzymes in combination with NADPH co-factor and cytochrome P450 enzymes in combination with the NADPH regenerating system.

20. The method of claim 19, wherein the neutral loss mass spectrum is measured using ESI-MS/MS or LS/MS.

21. A mixture comprising a compound of formula (I)

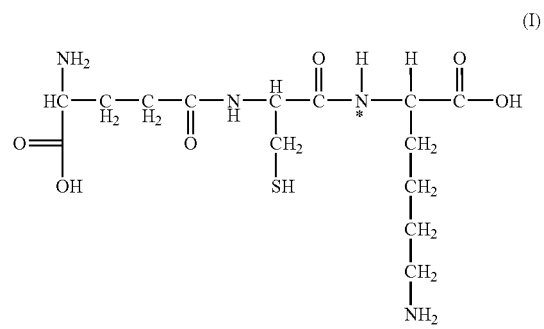

(I)

and an isotopically labeled compound of formula (I)

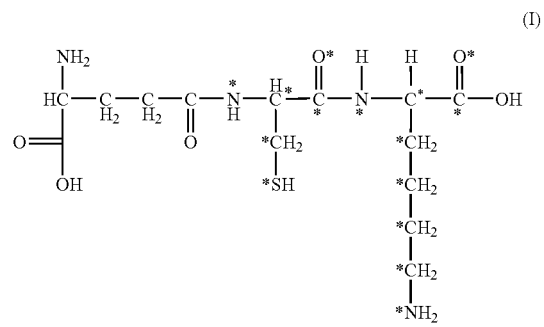

(I)

wherein one or more of the carbon, nitrogen, oxygen, sulfur or non-exchangeable hydrogen atoms on the starred groups are isotopically enriched.

22. The mixture of claim 21, wherein the molar ratio of the compound of formula (I) to the isotopically labeled compound of formula (I) is about 1:1.

23. The mixture of claim 22, wherein the isotopically labeled compound of formula (I) is labeled with six $^{13}C$ atoms and two $^{15}N$ atoms.

24. A mixture comprising
  (a) a covalently bonded complex of a reactive metabolite and a compound of formula (I)

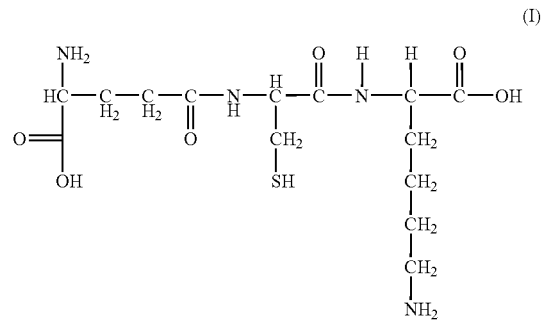

(I)

and (b) a covalently bonded complex of a reactive metabolite and an isotopically labeled compound of formula (I)

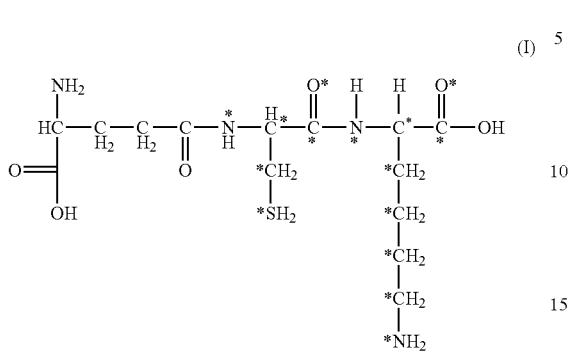
(I)

wherein one or more of the carbon, nitrogen, oxygen, sulfur or non-exchangeable hydrogen atoms on the starred groups are isotopically enriched.

25. The mixture of claim 24, wherein the isotopically labeled compound of formula (I) is a compound of formula (I-IS)

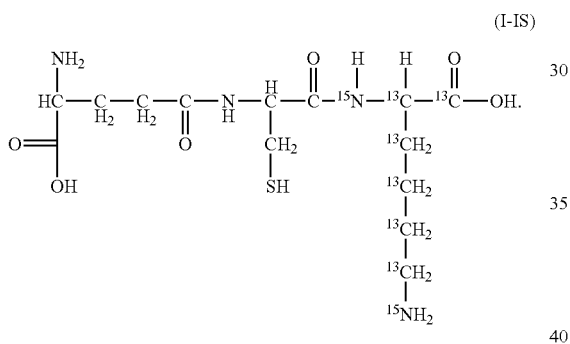
(I-IS)

26. The mixture of claim 24, wherein the molar ratio of the covalently bonded complex of a reactive metabolite and non-isotopically labeled compound of formula (I) and the covalently bonded complex of a reactive metabolite and isotopically labeled compound of formula (I) is about 1:1.

27. A method for detecting reactive metabolites of a test compound comprising (a) incubating a test compound with a mixture comprising a compound of formula (I),

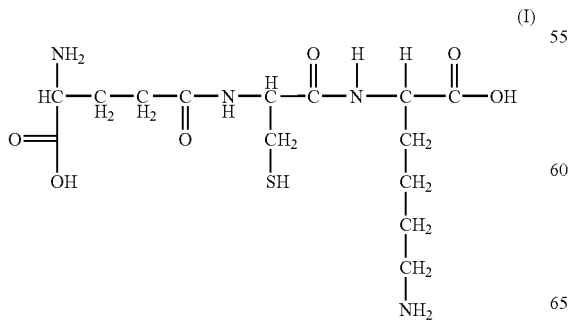
(I)

an isotopically-labeled compound of formula (I-IS)

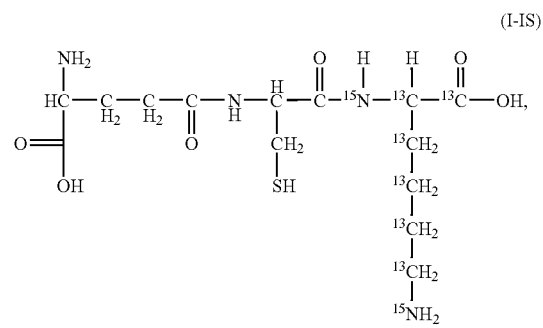
(I-IS)

and a drug metabolizing enzyme;
to yield a product mixture comprising one or more adducts;
(b) measuring a neutral loss mass spectrum of the one or more adducts produced in step (a); and
(c) detecting one or more isotopic doublets in the neutral loss mass spectrum of step (b), wherein the isotopic doublets differ in mass by 8 Da.

28. A method for detecting reactive metabolites of a test compound comprising

Step A: incubating a mixture comprising
(a) a test compound;
(b) a compound of formula (I)

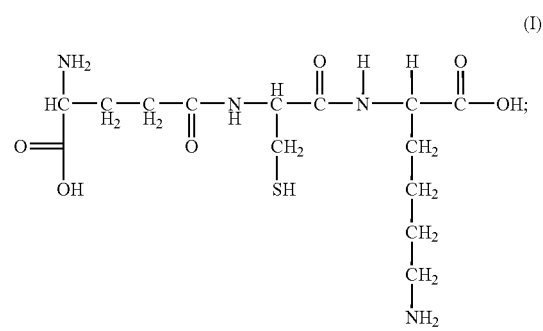
(I)

(c) an isotopically labeled compound of formula (I-IS)

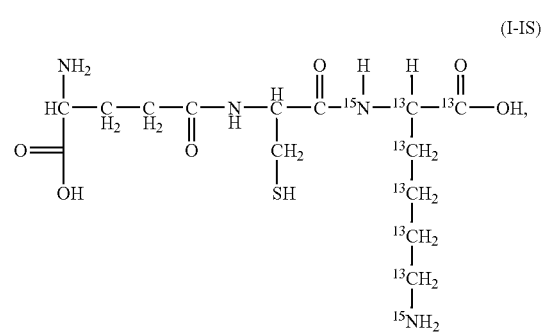
(I-IS)

wherein the molar ratio of the compound of formula (I) to the isotopically labeled compound of formula (I-IS) is about 1:1; and
(c) a drug metabolizing enzyme selected from the group consisting of human liver microsomes, cytochrome P450 enzymes in combination with NADPH co-factor and cytochrome P450 enzymes in combination with NADPH regenerating system;

to yield a product mixture comprising one or more incubation products selected from the group consisting of (a) a non-reactive metabolite;

(b) an adduct formed between the compound of formula (I) and a reactive metabolite; and (c) an adduct formed between the isotopically labeled compound of formula (I-IS) and a reactive metabolite;

Step B: measuring a neutral loss mass spectrum of the product mixture produced in Step (A); and Step C: detecting one or more isotopic doublets in a neutral loss mass spectrum of Step (B), wherein the isotopic doublets differ in mass by 8 Da.

29. A method for detecting reactive metabolites of a test compound comprising (a) incubating a test compound with a mixture comprising a non-isotopically labeled compound of formula (I)

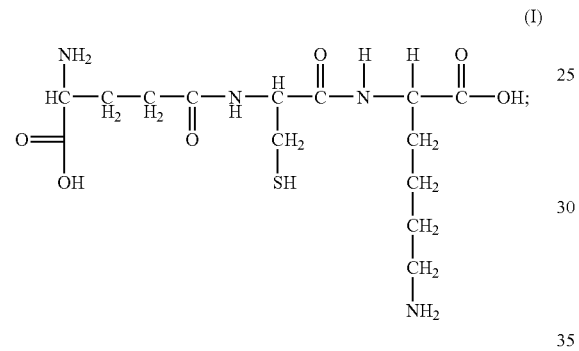

an isotopically labeled compound of formula (I)

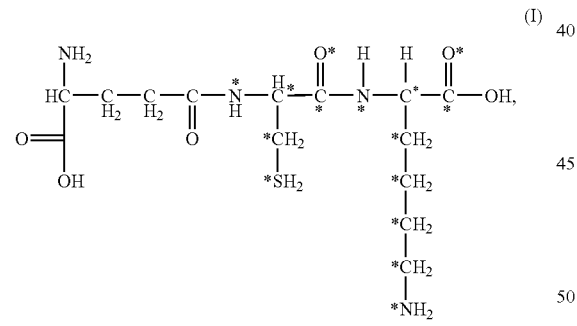

wherein one or more of the carbon, nitrogen, oxygen, sulfur and/or non-exchangeable hydrogen atoms on the starred groups are isotopically enriched;

and a drug metabolizing enzyme to yield a product mixture comprising one or more adducts;

(b) separating the one or more adducts of step (a);

(c) measuring a neutral loss mass spectrum of said separated adducts;

(d) detecting one or more isotopic doublets in the neutral loss mass spectrum of said separated adducts, wherein the doublet differs in mass by the difference in mass between the non-isotopically labeled compound of formula (I) and the isotopically labeled compound of formula (I).

30. A method for detecting reactive metabolites of a test compound comprising (a) incubating a test compound with a mixture comprising a non-isotopically labeled compound of formula (I)

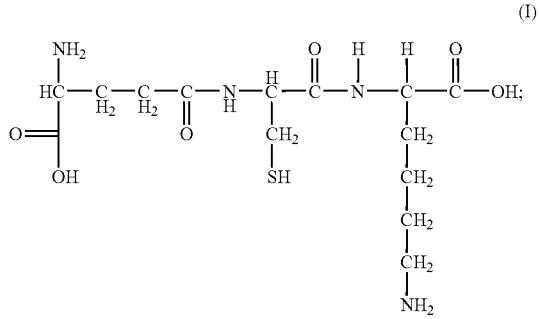

an isotopically labeled compound of formula (I-IS)

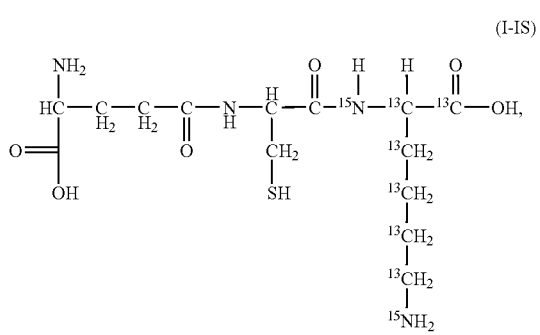

wherein the molar ratio of the compound of formula (I) to the isotopically labeled compound of formula (I-IS) is about 1:1;

and a drug metabolizing enzyme to yield a product mixture comprising one or more adducts;

(b) separating the one or more adducts of step (a);

(c) measuring a neutral loss mass spectrum of said separated adducts;

(d) detecting one or more isotopic doublets in the neutral loss mass spectrum of said separated adducts, wherein the doublet differs in mass by 8 Da.

31. A method for identifying a drug candidate comprising (a) incubating a test compound with a mixture comprising a non-isotopically labeled compound of formula (I)

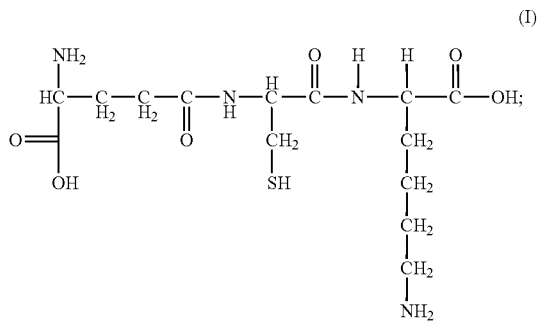

an isotopically labeled compound of formula (I)

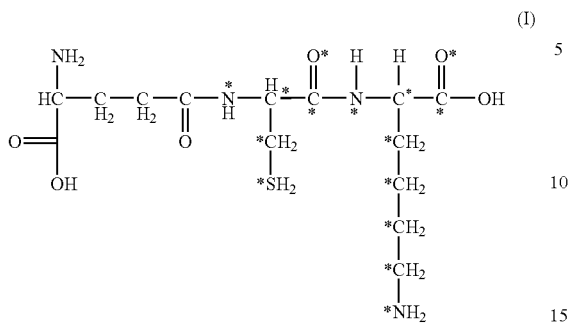
(I)

wherein one or more of the carbon, nitrogen, oxygen, sulfur or non-exchangeable hydrogen atoms on the starred groups are isotopically enriched;

and a drug metabolizing enzyme; to yield a product mixture;

(b) measuring a neutral loss mass spectrum of the product mixture produced in Step (a); and (c) detecting the absence of isotopic doublets in the neutral loss mass spectrum of Step (b).

32. The method of claim 31, wherein the isotopically labeled compound of formula (I) is labeled with six $^{13}$C atoms and two $^{15}$N atoms.

33. The method of claim 32, wherein the molar ratio of the compound of formula (I) to the isotopically labeled compound of formula (I) is about 1:1.

34. The method of claim 33, wherein the drug metabolizing enzyme is cytochrome P450 enzymes in combination with NADPH co-factor or cytochrome P450 enzymes in combination with NADPH regenerating system.

35. The method of claim 34, wherein the neutral loss mass spectrum is measured using ESI-MS/MS or LS/MS.

36. A method for identifying a drug candidate comprising (a) incubating a test compound with a mixture comprising a non-isotopically labeled compound of formula (I)

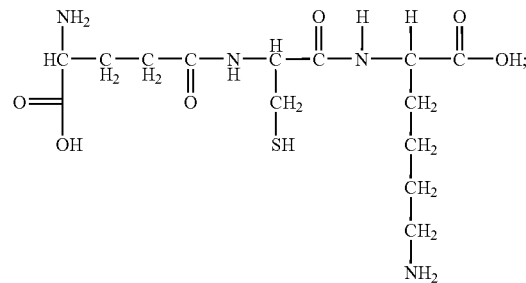
(I)

an isotopically labeled compound of formula (I-IS)

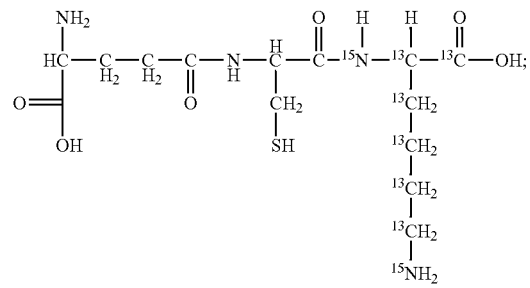
(I-IS)

and a drug metabolizing enzyme; to yield a product mixture;

(b) measuring a neutral loss mass spectrum of the product mixture produced in Step (a); and (c) detecting the absence of isotopic doublets in the neutral loss mass spectrum of Step (b).

37. The method of claim 36, wherein the molar ratio of the compound of formula (I) to the isotopically labeled compound of formula (I) is about 1:1.

38. The method of claim 37, wherein the drug metabolizing enzyme is cytochrome P450 enzymes in combination with NADPH co-factor or cytochrome P450 enzymes in combination with NADPH regenerating system.

39. The method of claim 38, wherein the neutral loss mass spectrum is measured using ESI-MS/MS or LS/MS.

\* \* \* \* \*